(12) United States Patent
Rozsumberszki et al.

(10) Patent No.: US 11,958,798 B2
(45) Date of Patent: Apr. 16, 2024

(54) PROCESS FOR THE PREPARATION OF ILOPROST

(71) Applicant: CHINOIN GYÓGYSZER ÉS VEGYÉSZETI TERMÉKEK GYÁRA ZRT., Budapest (HU)

(72) Inventors: Imre Rozsumberszki, Budapest (HU); Zsuzsanna Kardos, Budapest (HU); Irén Hortobágyi, Budapest (HU); Tibor Szabó, Budapest (HU); Csaba Váradi, Budapest (HU); Tamás Bán, Budapest (HU)

(73) Assignee: EUROAPI HUNGARY LIMITED LIABILITY COMPANY, Budapest (HU)

( * ) Notice: Subject to any disclaimer, the term of this patent is extended or adjusted under 35 U.S.C. 154(b) by 0 days.

(21) Appl. No.: 17/973,129

(22) Filed: Oct. 25, 2022

(65) Prior Publication Data

US 2023/0115500 A1    Apr. 13, 2023

Related U.S. Application Data

(62) Division of application No. 17/048,053, filed as application No. PCT/HU2019/050016 on Apr. 16, 2019, now Pat. No. 11,535,580.

(30) Foreign Application Priority Data

Apr. 16, 2018   (HU) .................................... P1800125

(51) Int. Cl.
    *C07C 51/09*    (2006.01)
    *C07C 67/31*    (2006.01)
    (Continued)

(52) U.S. Cl.
    CPC .............. *C07C 51/09* (2013.01); *C07C 67/31* (2013.01); *C07B 2200/13* (2013.01);
    (Continued)

(58) Field of Classification Search
    CPC . C07B 2200/13; C07C 2602/22; C07C 51/09; C07C 59/46; C07C 67/31;
    (Continued)

(56) References Cited

U.S. PATENT DOCUMENTS 4,879,285 A   11/1989   O'Neill
5,425,853 A   6/1995   Berg

OTHER PUBLICATIONS

Steiner et al. (A Side Chain of Diastereomeric Iloprost Protrudes From the Cage in the Complex With Cyclomaltoheptaose (β-Cyclodextrin): Crystal Structure of (β-Cyclodextrin)2 Iloprost . 20.5 H2O, Carbohydrate Research, 192, pp. 43-49, Published 1989) (Year: 1989).*

(Continued)

*Primary Examiner* — Yevgeny Valenrod
*Assistant Examiner* — Blaine G Doletski
(74) *Attorney, Agent, or Firm* — Birch, Stewart, Kolasch & Birch, LLP

(57) ABSTRACT

The present invention relates to a process for the preparation of iloprost of formula I through new intermediates, isolation of iloprost of formula I in solid form, as well as preparation of the 16(S)-iloprost and 16(R)-iloprost isomers of formulae (S)-I and (R)-I and isolation of iloprost of formula I and 16(S)-iloprost of formula (S)-I in solid, crystalline form.

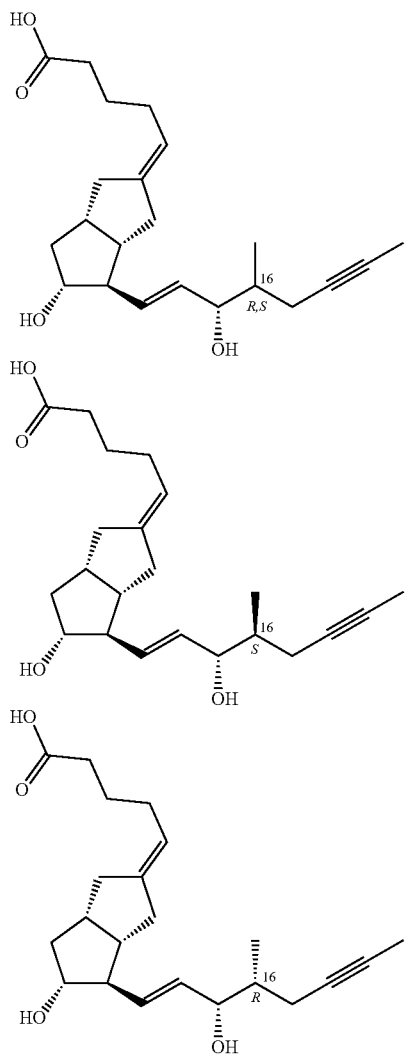

5 Claims, 9 Drawing Sheets

Figure 1:
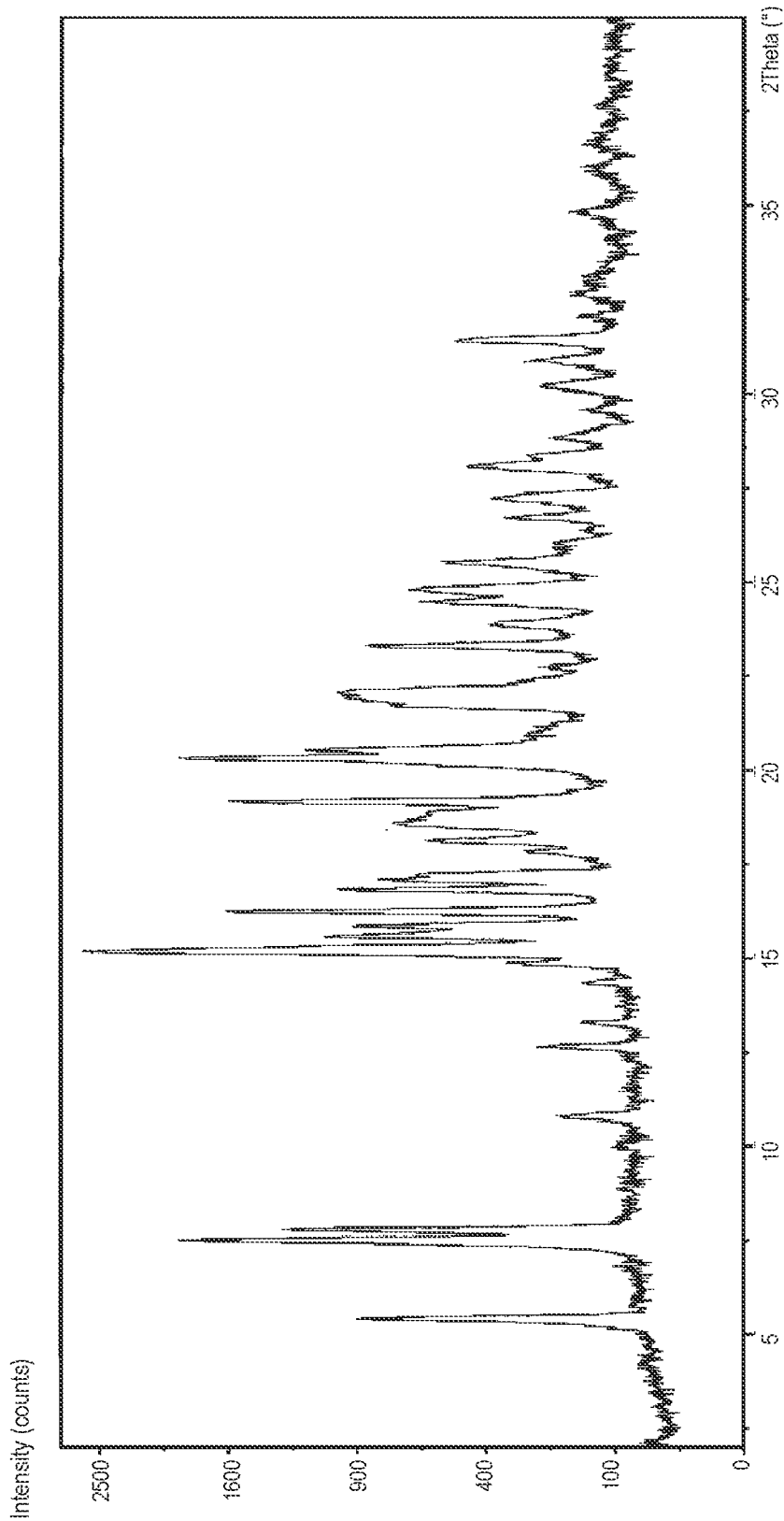

(51) Int. Cl.
*C07C 59/46* (2006.01)
*C07C 69/608* (2006.01)

(52) U.S. Cl.
CPC ............ *C07C 59/46* (2013.01); *C07C 69/608* (2013.01); *C07C 2602/22* (2017.05)

(58) Field of Classification Search
CPC ....... C07C 69/608; C07C 13/44; C07C 67/48; A61K 31/5575; C07D 309/10; C07D 309/12
See application file for complete search history.

(56) References Cited

OTHER PUBLICATIONS

Tocris (Certificate of Analysis, pp. 1-2, Published Jan. 2016) (Year: 2016).*
Notice of Allowance issued in U.S. Appl. No. 17/048,053, dated Jul. 25, 2022.
Restriction/Election Requirement issued in U.S. Appl. No. 17/048,053, dated Mar. 28, 2022.
Skuballa et al. (Chemistry of stable prostacyclin analogs: synthesis of iloprost, pp. 17-24, Published 1987. As cited as reference D1 in the Written Opinion for PCT/HU2019/050016). (Year: 1987).

* cited by examiner

| Numbering | $^{13}C$ (ppm) | $^1H$ (ppm) | Number of $^1H$ | Multiplicity | Coupling constant (Hz) |
|---|---|---|---|---|---|
| 1 | 175,4 | - | | | |
| 2 | 34,1 | 2,23 | 2 | t | $J_{2,3}$=7,4 |
| 3 | 25,8 | 1,57 | 2 | m | |
| 4 | 29,3 | 2,00 | 2 | m | |
| 5 | 121,4 | 5,24 | 1 | t | $J_{4,5}$=7,1 |
| 6 | 143,48; 143,46 | - | | | |
| 7 | 38,84; 38,82 | 2,37; 1,98 | 2 | m | |
| 8 | 45,5 | 2,05 | 1 | m | |
| 9 | 38,0 | 2,37 | 1 | m | |
| 10 | 43,06; 43,04 | 2,18; 1,09 | 2 | m | |
| 11; OH | 77,3 | 3,59; 4,60 | 1; 1 | m | |
| 12 | 56,82; 56,80 | 1,75 | 1 | m | |
| 13 | 133,3; 133,8 | 5,53; 5,50 | 1 | dd | $J_{12,13}$=6,4 |
| 14 | 133,1; 133,0 | 5,39; 5,37 | 1 | dd | $J_{13,14}$=15,4 |
| 15; OH | 75,1; 74,4 | 3,90; 3,77; 4,66; 4,62 | 1; 1 | t | $J_{14,15}$=6,0 |
| 16 | 39,8; 39,6 | 1,60; 1,58 | 1 | m | |
| 17 | 22,8; 22,5 | 2,26; 2,00; 2,24; 1,91 | 2 | m | |
| 18 | 77,2; 77,1 | - | | | |
| 19 | 79,5; 79,3 | - | | | |
| 20 | 4,1 | 1,77 | 3 | s | |
| 24 | 16,4; 15,6 | 0,92; 0,89 | 3 | d | $J_{16,24}$=6,8 |
| 25 | 36,5 | 2,31; 2,03 | 2 | m | |

| Numbering | $^{13}$C (ppm) | $^1$H (ppm) | Number of $^1$H |
|---|---|---|---|
| 1 | 174,2 | - | |
| 2 | 33,6 | 2,34 | 2 |
| 3 | 25,64; 25,62 | 1,62 | 2 |
| 4 | 29,1 | 2,01 | 2 |
| 5 | 121,79; 121,76 | 5,27 | 1 |
| 6 | 142,96; 142,93 | - | |
| 7 | 38,72; 38,65 | 2,37; 2,00 | 2 |
| 8 | 45,1 | 2,23; 2,25 | 1 |
| 9 | 38,5; 38,4 | 2,48; 2,33 | 1 |
| 10 | 41,3; 39,1 | 2,39; 2,32; 1,27; 1,11 | 2 |
| 11 | 83,0; 80,1 | 3,95; 3,90 | 1 |
| 12 | 55,79; 55,78; 54,98; 54,96 | 2,16; 2,11 | 1 |
| 13 | 149,88; 149,76; 149,76; 149,68 | 6,88; 6,85 | 1 |
| 14 | 129,53; 129,49; 129,45; 129,13 | 6,28; 6.25 | 1 |
| 15 | 202,10; 202,06; 202,04; 202,03 | - | |
| 16 | 43,42; 43,38; 43,23; 43,18 | 3,00; 2,98 | 1 |
| 17 | 22,59; 22,56 | 2,38; 2,24 | 2 |
| 18 | 78,12; 78,10; 78,07; 78,05 | - | |
| 19 | 77,76; 77,75; 77,74; 77,70 | - | |
| 20 | 4,0 | 1,74 | 3 |
| 24 | 17,15; 17,13 | 1,10; 1,08 | 3 |
| 25 | 36,1; 36,0 | 2,32; 2,07 | 2 |
| 26 | 52,1 | 3,62 | 3 |
| e | 99,30; 96,8 | 4,64; 4,56 | 1 |
| d | 31,3; 31,2 | 1,60; 1,56; 1,44; 1,40 | 2 |
| c | 20,2; 19,8 | 1,71; 1,68; 1,48; 1,44 | 2 |
| b | 26,0; 25,9 | 1,62; 1,60; 1,47; 1,42 | 2 |
| a | 62,5; 61,9 | 3,77; 3,68; 3,42; 3,39 | 2 |

Figure 7

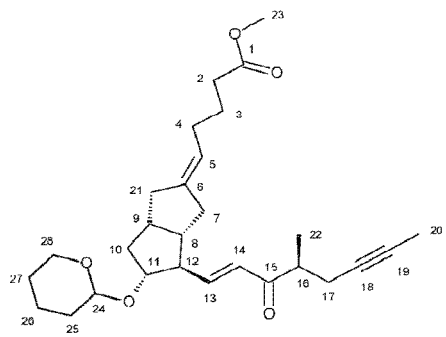

| Numbering | $^{13}$C (ppm) | $^{1}$H (ppm) | Number of $^{1}$H | Multiplicity | Coupling constant (Hz) (+/- 0.2Hz) |
|---|---|---|---|---|---|
| 1 | 173.23 | - | - | - | |
| 2 | 32.63 | 2.30*; 2.295* | 2 | m (t) | $J_{2,3}$=7.4 |
| 3 | 24.67$; 24.65$ | 1.575** | 2 | m (qui) | $J_{3,4}$=7.2 |
| 4 | 28.14 | 1.975*** | 2 | m | |
| 5 | 120.77$; 120.80$ | 5.23+ | 1 | t | $J_{4,5}$=6.7 |
| 6 | 141.99$; 141.96$ | - | - | - | |
| 7 | 37.69$; 37.76$ | β: 2.33*<br>α: 1.99***; 1.95*** | 1<br>1 | m<br>m | |
| 8 | 44.17$; 44.19$ | 2.20* | 1 | m | |
| 9 | 37.50$; 37.59$ | 2.445++ | 1 | m | |
| 10 | 40.31; 38.14 | β: 2.28*; 2.35*<br>α: 1.235+++; 1.075# | 1<br>1 | m<br>m (ddd) | $J_{10gem}$=12.6; $J_{9,10β}$=8.2 |
| 11 | 82.02, 79.21 | 3.86##; 3.905## | 1 | m (td) | $J_{10β,11}$=$J_{11,12}$=9.3/9.2; $J_{10α,11}$=7.0/6.7 |
| 12 | 54.83; 54.00 | 2.075***; 2.125*** | 1 | m (q) | 9.2/9.0 |
| 13 | 148.74; 148.86 | 6.83###; 6.74### | 1 | m (dd) | $J_{12,13}$=8.7/8.3; $J_{13,14}$=15.7 |
| 14 | 128.50$; 128.54$ | 6.22&; 6.24& | 1 | m (d) | |
| 15 | 201.04$; 201.08$ | - | - | - | |
| 16 | 42.27$; 42.21$ | 2.96&&; 2.965&& | 1 | m (sex) | $J_{16,17}$=$J_{16,22}$=6.9 |
| 17 | 21.60$; 21.62$ | a: 2.34*<br>b: 2.19* | 1<br>1 | m<br>m | |
| 18 | 77.06$; 77.08$ | - | - | - | |
| 19 | 76.76$; 76.75$ | - | - | - | |
| 20 | 3.02 | 1.70&&& | 3 | m (t) | $J_{17,20}$=2.4 |
| 21 | 35.07$; 35.12$ | β: 2.285*<br>α: 2.03*** | 1<br>1 | m<br>m | |
| 22 | 16.16 | 1.05#; 1.055# | 3 | m (d) | |
| 23 | 51.10 | 3.58ʟ; 3.575ʟ | 3 | m (s) | |
| 24 | 98.34; 95.81 | 4.525ʟʟ; 4.605ʟʟʟ | 1 | m (dd) | ~4.1/~3.6; ~2.6 |
| 25 | 30.28$; 30.38$ | a: 1.55**<br>b: 1.40ɪ | 1<br>1 | m<br>m | |
| 26 | 19.20; 18.79 | a: 1.665&&&; 1.645&&&<br>b: 1.41ɪ; 1.44ɪ | 1<br>1 | m<br>m | |
| 27 | 24.96$; 25.02$ | a: 1.44ɪ<br>b: 1.38ɪ | 1<br>1 | m<br>m | |
| 28 | 61.57; 60.89 | a: 3.73ⅲ; 3.65ⅲ<br>b: 3.38ⅲ; 3.345ⅲ | 1<br>1 | m<br>m | |

$: Partly overlapped $^{13}$C NMR signals. *, , *, #, ##, ###, &, &&, &&&, ʟ, ɪ, ⅲ: Partly overlapped $^{1}$H NMR signals. ***, +, +++, #, &, ʟ, ʟʟ, ʟʟʟ, ⅲ: Partly overlapped by the $^{1}$H NMR signals of the sample impurities. ++: Partly overlapped by the $^{1}$H NMR signals of the DMSO-d$_6$ solvent.

Figure 8

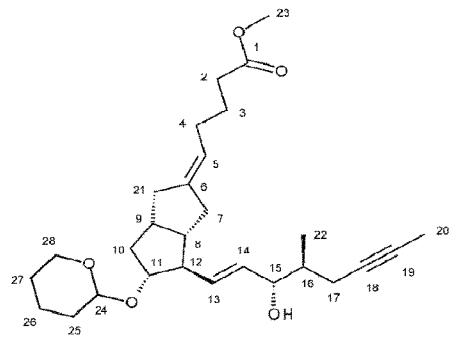

| Numbering | $^{13}$C (ppm) | $^{1}$H (ppm) | Number of $^{1}$H | Multiplicity | Coupling constant (Hz) (+/- 0.2Hz) |
|---|---|---|---|---|---|
| 1 | 173.24 | - | - | - | |
| 2 | 32.63 | 2.285* | 2 | m (t) | $J_{2,3}$=7.3 |
| 3 | 24.68$; 24.65$ | 1.57** | 2 | m (qui) | $J_{3,4}$=7.3 |
| 4 | 28.16 | 1.965*** | 2 | m | |
| 5 | 120.45 | 5.205 | 1 | t | $J_{4,5}$=6.3 |
| 6 | 142.43$; 142.40$ | - | - | - | |
| 7 | 37.71$; 37.82$ | β: 2.32* <br> α: 1.98***; 1.95*** | 1 <br> 1 | m <br> m | |
| 8 | 44.42 | 2.06*** | 1 | m | |
| 9 | 37.09; 37.30 | 2.38* | 1 | m | |
| 10 | 40.16; 37.68$ | β: 2.225*; 2.30* <br> α: 1.17⁺; 0.995⁺⁺ | 1 <br> 1 | m <br> m (ddd) | $J_{10gem}$=12.5/12.1; $J_{9,10α}$=8.0/7.6 |
| 11 | 82.40; 78.77 | 3.67; 3.76⁺⁺⁺ | 1 | td / m (td) | $J_{10β,11}$=$J_{11,12}$=9.3/9.0; $J_{10α,11}$=7.1/7.0 |
| 12 | 54.48; 53.43 | 1.85***; 1.92*** | 1 | m (td) | $J_{12,13}$=8.1/7.7 |
| 13 | 131.88; 131.77 | 5.50#; 5.52# | 1 | m (dd) | $J_{13,14}$=15.6/15.4 |
| 14 | 132.22; 132.05 | 5.37##; 5.40## | 1 | m (dd) | $J_{14,15}$=6.1 |
| 15 | 73.37; 73.53 | 3.78⁺⁺⁺; 3.79⁺⁺⁺ | 1 | m / m (q/dt) | ~5.5 |
| OH-15 | | 4.65###; 4.645### | 1 | m (d) | $J_{15,15-OH}$=5.0/4.9 |
| 16 | 38.75$; 38.82$ | 1.555** | 1 | m | |
| 17 | 21.43 | a: 2.205* <br> b: 1.945*** | 1 <br> 1 | m <br> m | |
| 18 | 78.21$; 78.28$ | - | - | - | |
| 19 | 76.13$; 76.06$ | - | - | - | |
| 20 | 3.12 | 1.73& | 3 | m (t) | $J_{17,20}$=2.2 |
| 21 | 35.40$; 35.45$ | β: 2.285* <br> α: 1.995*** | 1 <br> 1 | m <br> m | |
| 22 | 15.28$; 15.31$ | 0.85&&; 0.86&& | 3 | m (d) | $J_{16,22}$=6.9 |
| 23 | 51.10 | 3.58&&&; 3.575&&& | 3 | m (s) | |
| 24 | 98.39; 95.08 | 4.59###; 4.61### | 1 | m (dd) / m (t) | ~4.2; ~2.6/~3.2 |
| 25 | 30.38$ | a: 1.55** <br> b: 1.405ᴸ | 1 <br> 1 | m <br> m | |
| 26 | 19.24; 18.60 | a: 1.66&; 1.69& <br> b: 1.41ᴸ; 1.44ᴸ | 1 <br> 1 | m <br> m | |
| 27 | 25.05$; 25.10$ | a: 1.44ᴸ <br> b: 1.395ᴸ | 1 <br> 1 | m <br> m | |
| 28 | 61.47; 60.64 | a: 3.73⁺⁺⁺; 3.745⁺⁺⁺ <br> b: 3.385ᴸᴸ; 3.36ᴸᴸ | 1 <br> 1 | m <br> m | |

$: Partly overlapped $^{13}$C NMR signals. *, , *, ⁺, ⁺⁺, #, ##, ###, &, &&, &&&, ᴸ, ᴸᴸ: Partly overlapped $^{1}$H NMR signals. ***, ⁺, ⁺⁺, #, ##, &&,
ᴸ: Partly overlapped by the $^{1}$H NMR signals of the sample impurities.

Figure 9

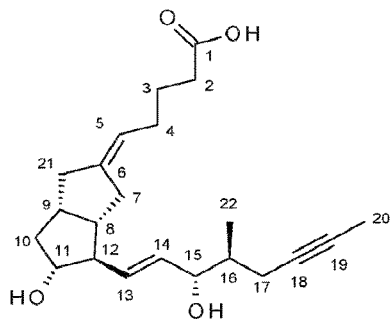

| Numbering | $^{13}C$ (ppm) | $^1H$ (ppm) | Number of $^1H$ | Multiplicity | Coupling constant (Hz) (+/- 0.2Hz) |
|---|---|---|---|---|---|
| 1 | 174.44 | - | - | - | |
| COOH-1 | | 11.945 | 1 | br | |
| 2 | 33.15 | 2.19* | 2 | m (t) | $J_{2,3}=7.3$ |
| 3 | 24.90 | 1.535** | 2 | m (qui) | $J_{3,4}=7.3$ |
| 4 | 28.33 | 1.965*** | 2 | m | |
| 5 | 120.45 | 5.205 | 1 | t | $J_{4,5}=6.3$ |
| 6 | 142.53 | - | - | - | |
| 7 | 37.87 | β: 2.305* | 1 | m | |
| | | α: 1.945*** | 1 | m | |
| 8 | 44.58 | 2.02*** | 1 | m | |
| 9 | 37.07 | 2.34* | 1 | m | |
| 10 | 42.08 | β: 2.14* | 1 | m (dt) | $J_{10gem}=12.3$; $J_{9,10β}=7.5$ |
| | | α: 1.055 | 1 | m (ddd) | $J_{9,10α}=7.9$ |
| 11 | 76.37 | 3.555⁺ | 1 | td | $J_{10β,11}=J_{11,12}=9.2$, $J_{10α,11}=7.2$ |
| OH-11 | | 4.54⁺⁺ | 1 | br | |
| 12 | 55.86 | 1.715⁺⁺⁺ | 1 | m (td) | $J_{8,12}=9.2$ |
| 13 | 132.85 | 5.47# | 1 | dd | $J_{12,13}=7.5$; $J_{13,14}=15.4$ |
| 14 | 131.98 | 5.33## | 1 | dd | $J_{14,15}=6.9$ |
| 15 | 74.18 | 3.735 | 1 | t (dd) | $J_{15,16}$~5.9 |
| OH-15 | | 4.60⁺⁺ | 1 | br | |
| 16 | 38.68 | 1.545** | 1 | m | |
| 17 | 21.58 | a: 2.215* | 1 | m | |
| | | b: 1.955*** | 1 | m | |
| 18 | 78.34 | - | - | - | |
| 19 | 76.20$ | - | - | - | |
| 20 | 3.18 | 1.735⁺⁺⁺ | 3 | m (t) | $J_{17,20}=2.4$ |
| 21 | 35.58 | β: 2.285* | 1 | m | |
| | | α: 1.99*** | 1 | m | |
| 22 | 15.44 | 0.85### | 3 | m (d) | $J_{16,22}=6.7$ |

$: Partly overlapped by the $^{13}C$ NMR signals of the 16-R-ILO-12 isomer. *, , *, ⁺⁺, ⁺⁺⁺: Partly overlapped $^1H$ NMR signals. #, ##, ###: Partly overlapped by the $^1H$ NMR signals of the 16-R-ILO-12 isomer. ⁺: Partly overlapped by the $^1H$ NMR signal of water.

PROCESS FOR THE PREPARATION OF ILOPROST

This application is a Divisional of co-pending application Ser. No. 17/048,053, filed on Oct. 15, 2020, which is the National Stage Application under 35 U.S.C. § 371 of International Application No. PCT/HU2019/050016, filed on Apr. 16, 2019, which claims the benefit under 35 U.S.C. § 119(a) to Hungarian Patent Application No. P1800125, filed on Apr. 16, 2018, all of which are hereby expressly incorporated by reference into the present application.

The subject of our invention is a process for the preparation of iloprost of formula I through new intermediates, isolation of iloprost in solid form, as well as preparation of the 16(S)-iloprost and 16(R)-iloprost isomers of formulae (S)-I and (R)-I and isolation of the 16(S)-iloprost of formula (S)-I in solid, crystalline form.

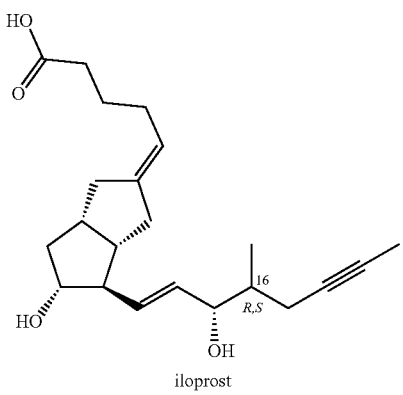

iloprost   I

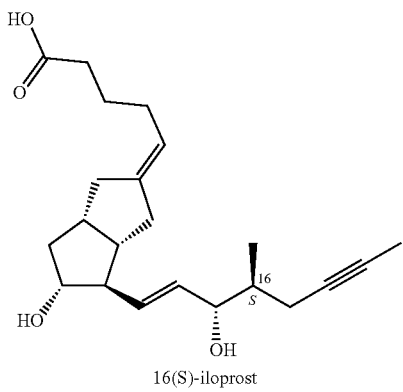

16(S)-iloprost   (S)-I

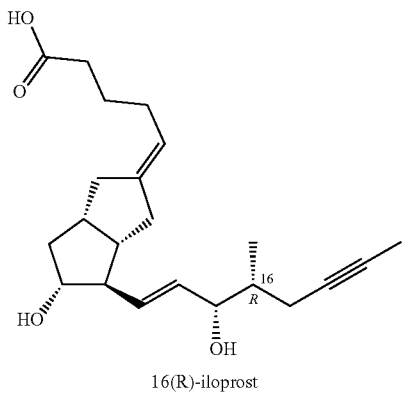

16(R)-iloprost   (R)-I

PRIOR ART

Iloprost is a carbacyclin derivative. The carbacyclin skeleton is a modified prostacyclin, where the oxygen atom of the oxygen-containing five-membered ring is replaced with a carbon atom. Carbacyclins do not contain the very sensitive enol ether structural part, therefore they are chemically more stable than prostacyclins. Chemical and biochemical properties of the carbacyclin structure, as well as the early syntheses are summarized in publication R. C. Nickolson, M. H. Town, H. Vorbruggen, Prostacyclin-analogues, *Medicinal Research Reviews*, Vol. 1985, 5 (1), 1-53.

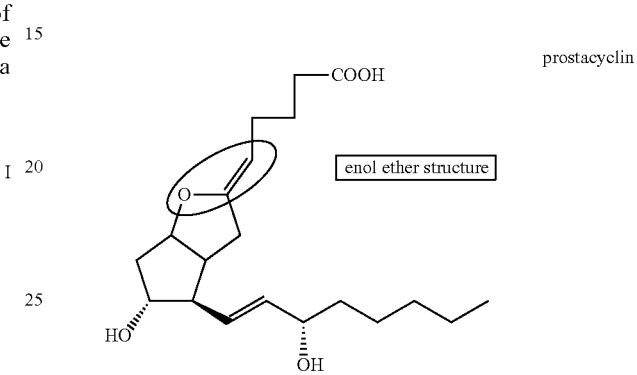

prostacyclin

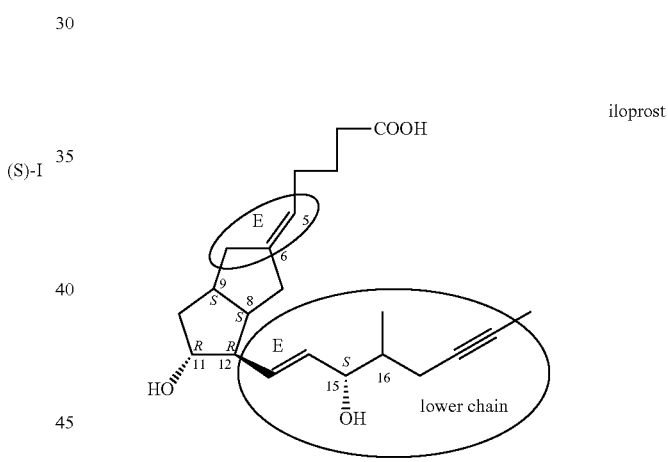

iloprost

Iloprost contains 6 asymmetric centres and it is an approximately 1:1 ratio mixture of two diastereoisomers, as the configuration of the carbon atom in position-16 may be (R) or (S) with respect to the steric position of the methyl group. Although, at present a nearly 1:1 ratio mixture of 16(R)-iloprost and 16(S)-iloprost is used in therapy, activities of the two isomers are different, 16(S)-iloprost is more effective (*Biochimica et Biophysica Acta*, Biomembranes 1988, 942(2), 220-6; Prostaglandins, 1992, 43, 255-261). Regulatory authorities are urging the development of 16(S)-iloprost to pharmaceutical active ingredient.

It is noted here, that the carbon atoms of the lower chain are in every case numbered according to the rules accepted in prostaglandin chemistry. This numbering in some cases differs from the Chemical Abstract (CAS) and IUPAC names. In the Examples for the hitherto known compounds CAS names, whereas for the new compounds IUPAC names are used.

iloprost diastereomers

16(S)-iloprost

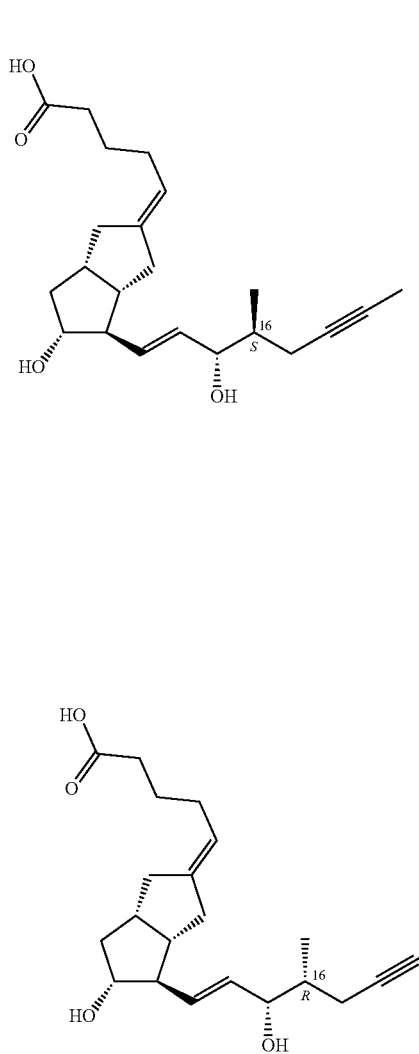

16(R)-iloprost

In the therapy iloprost is used to treat peripheral arterial diseases (peripheral arterial obstructive disease, PAOD) (1992, Bayer Schering Pharma) and pulmonary hypertension (2004, Bayer Schering Pharma).

The key-step of the iloprost syntheses is the construction of the appropriately substituted bicycle containing two five-membered rings.

Citations for the most frequent methods to prepare the appropriately substituted bicyclic ketone can be found in the latest publications which describe the synthesis of the optically active 16(S)-iloprost:

S. Chandrasekhar, Ch. Sridhar, P. Srihari, *Tetrahedron Asymmetry*, 2012, 23, 388-394;

H-J. Gais, G. J. Kramp, D. Wolters, L. R. Reddy, *Chem. Eur. J.*, 2006, 12, 5610-5617;

G. J. Kramp, M. Kim, H-J. Gais, C. Vermeeren, *J. Am. Chem. Soc.*, 2005, 127, 17910-17920.

The bicyclic ketone was synthesized by reacting glyoxal with dimethyl-1,3-aceto-dicarboxylate (A. Gawish, U. Weiss, *Org. Synth.*, 1986, 64, 27-38; H. Dahl (Schering AG), DE 3816801, J. A. Caedieux, D. J. Buller, P. D. Wilson, *Org. Lett.*, 2003, 5, 3983-3986). (Scheme 1)

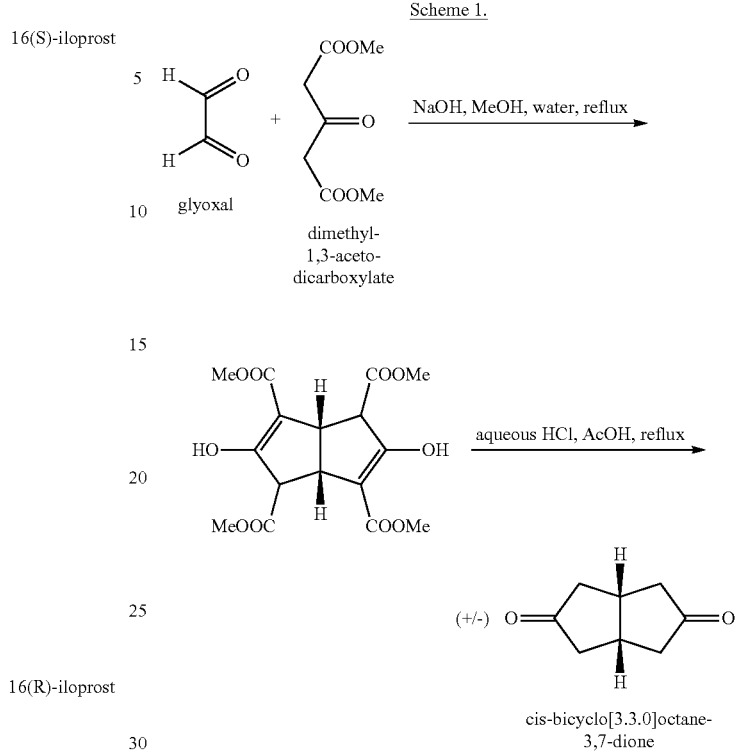

The cis-bicyclo[3.3.0]octane-3,7-dione was selectively ketalized with neopentyl glycol, the monoketal was reacted with dimethyl carbonate in the presence of sodium hydride, the oxo group was reduced, the alcohol was acetylated and the acetate was resolved by enzymatic hydrolysis (H. Dahl (Schering AG), DE 3816801). (Scheme 2)

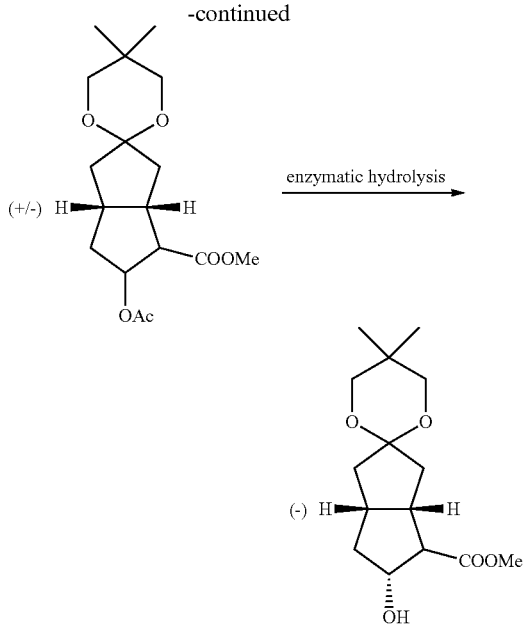

Researchers of Schering also worked out the enzymatic, selective mono-methoxycarbonylation of the monoketal disubstituted with methoxycarbonyl group (K. Petzoldt, H. Dahl, W. Skuballa, M. Gottwald, *Liebigs. Ann. Chem.*, 1990, 1087-1091). (Scheme 3)

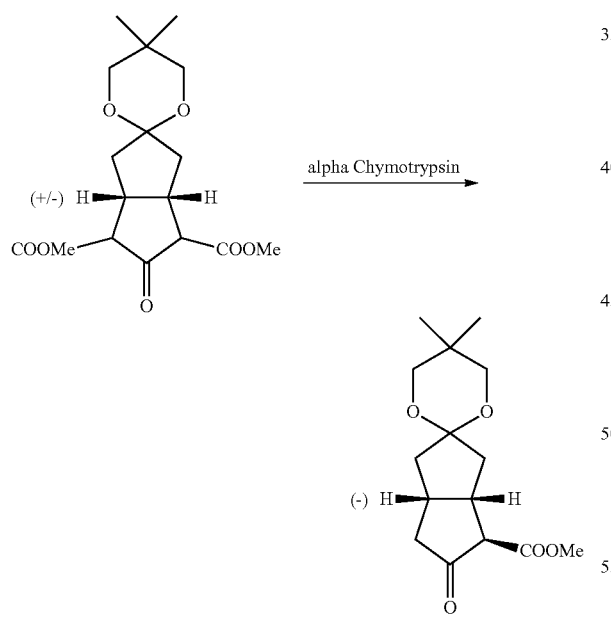

The appropriately substituted bicycle may also be formed from the appropriately substituted chiral Corey lactone, which is the most frequently used starting material for prostacyclin derivatives.

In the method of Skuballa and Vorbrüggen (*Angew. Chem. Int. Ed. Engl.*, 1981, 20, 1046-1048) the primary hydroxyl group of the Corey lactone containing benzoyl protecting group was protected with tert-butyldimethylsilyl chloride (TBDMSCl).

The TBDMS-benzoyl-Corey lactone was reacted with lithiated ethyl acetate in THF at (−)70° C., then water was eliminated from the resulting hydroxy ester. The benzoyl protecting group of the TBDMS-benzoyl-unsaturated ester was cleaved by methanolysis in the presence of potassium carbonate, the secondary hydroxyl group was converted to the oxo group by oxidation with chromium. The reactive enol ether ring of the TBDMS-unsaturated ester on treatment with 1,5-diazabicyclo[4.3.0]non-5-ene (DBN) underwent ring-opening and cyclisation to the ketone. The 11-oxo-group was reduced into the secondary alcohol group with sodium borohydride in one-pot reaction. Selectivity of the reduction was assured by neighbouring-group participation, but the epimeric purity was not given, although this is of key importance for the optical purity and for the amount of optical isomers. Summa yield of the ring-opening and the oxo group reduction was 70%. Ethoxycarbonyl group of the ethoxycarbonyl ketone was removed by reflux in aqueous toluene in the presence of 1,4-diazabicyclo[2.2.2]octane (DBO), the secondary hydroxyl group was protected with benzoyl group, the silyl protecting group of the primary hydroxyl group was cleaved. Summa yield of these three steps was 43%. (Scheme 4)

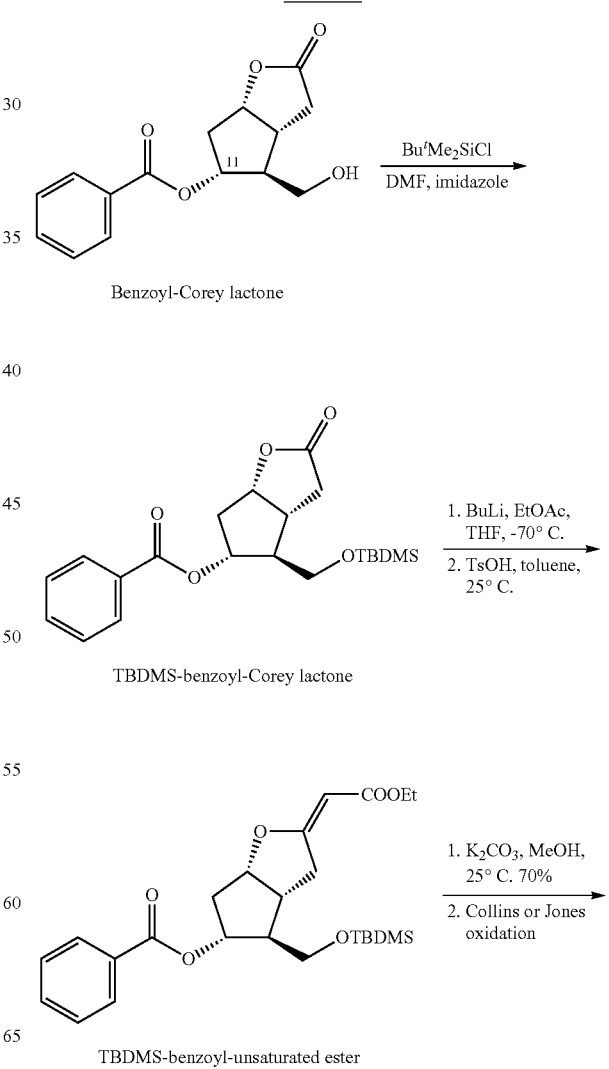

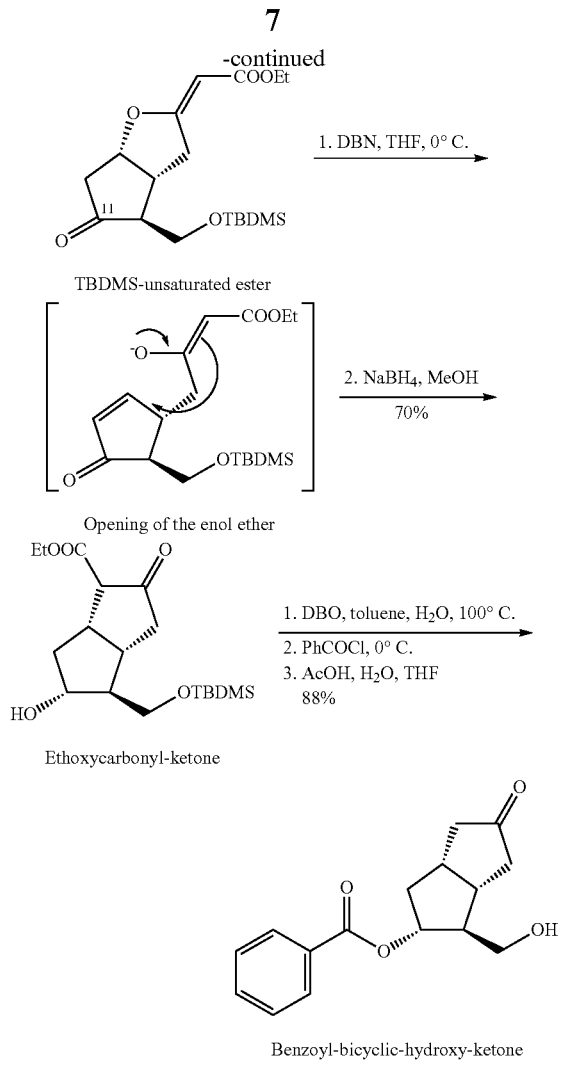

From the protected bicyclic hydroxy-ketone the lower and upper chains of iloprost may be formed by Wittig or modified Wittig reactions.

The advantage of the method is that the optically active bicyclic ketone intermediate, needed for the synthesis of carbacyclins, is formed starting from the optically active Corey lactone which is widely used in prostaglandin chemistry. Disadvantage is, however, that the reaction of Corey lactone with the lithium compound of ethyl acetate also gives numerous by-products, which significantly decrease the yield (in the referred publication the yield of that step is not given).

According to the Upjohn method (P. A. Aristoff, P. D. Johnson, A. W. Harrison, *J. Org. Chem.*, 1981, 46, 1954-1957) the protected Corey lactone, already containing the lower chain, is converted into the intermediate suitable for the preparation of carbacyclins.

In the first step the bis-THP-Corey lactone derivative (THP=tetrahydropyranyl) was treated with the lithium salt of dimethyl methylphosphonate (DMMP). The resulting bis-THP-hydroxy-phosphonate was oxidized by modified Collins oxidation into the bis-THP-keto-phosphonate. Intramolecular Horner-Wadsworth-Emmons (HWE) reaction of the bis-THP-keto-phosphonate provided the bis-THP-bicyclic enone. The double bond of the enone was saturated by transfer hydrogenation (bis-THP-bicyclic ketone), the THP protecting groups were then removed by acidic hydrolysis (bicyclic ketone). The upper chain of the bicyclic ketone, already containing the lower chain, was formed by Wittig reaction. The phosphoran needed for the reaction was prepared in situ from 4-carboxybutyltriphenylphosphonium bromide. The reaction, beside the desired product with the double bond of E-geometry (65%), also produced significant amount of Z-isomer (35%) (Scheme 5)

Scheme 5.

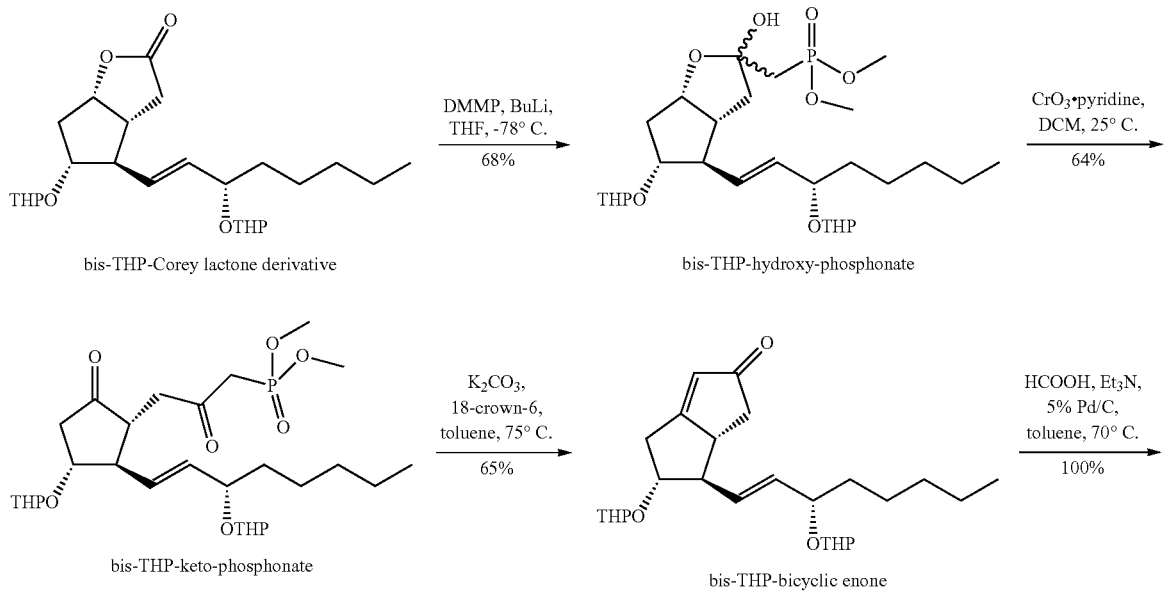

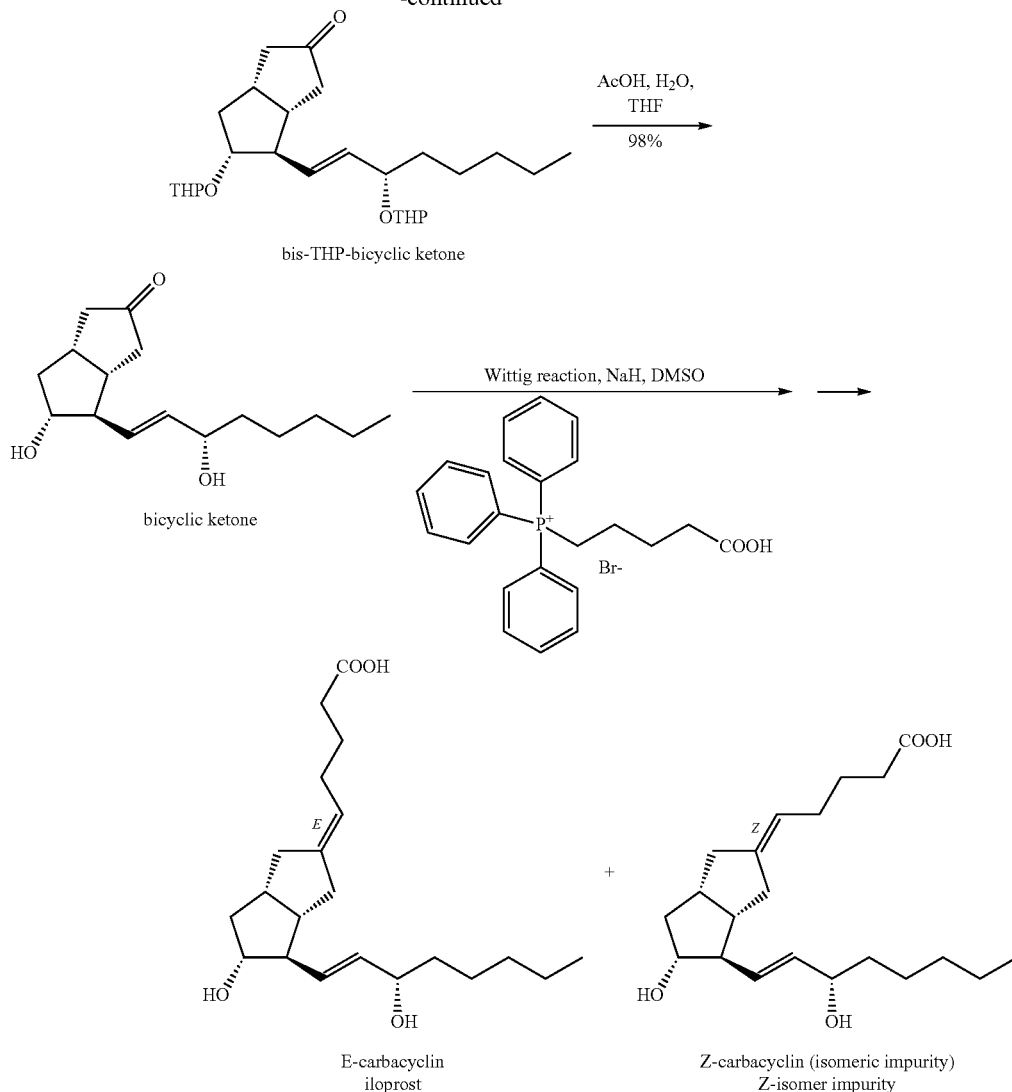

The process contains scalable steps with good yields, its disadvantage is that the formation of the upper chain is not selective, the product contains significant amount of Z-isomer contamination. In a later publication (P. A. Aristoff, P. D. Johnson, A. W. Harrison, *J. Org. Chem.*, 1983, 48, 5341-5348) the authors describe the above chemical steps with higher yields.

| Chemical step | *J. Org. Chem.*, 1981, 46, 1954 | *J. Org. Chem.*, 1983, 48, 5341 | Yield calculated for the desired intermediate in JOC publications | Chinoin process of the present application |
|---|---|---|---|---|
| a) formation of the phosphonate | 68% (20% starting material) | 99% (20% starting material) | 79% | 96% |
| b) oxidation | 64% (29% of eliminated product III)** | 64% (29% of eliminated product III)** | 35% | 63% (≤5% of eliminated product)** |

| Chemical step | J. Org. Chem., 1981, 46, 1954 | J. Org. Chem., 1983, 48, 5341 | Yield calculated for the desired intermediate in JOC publications | Chinoin process of the present application |
|---|---|---|---|---|
| c) HWE reaction | 65% | 77% | 77% | 65%* |
| Wittig reaction (E/Z isomer %) | | 65%:35% | | 60%:40% |
| Summa yield of II-VII | | | 21.3% | 39.3% |

*with recycling (together with the UV isomerization)
**structure of the eliminated product III is shown in Scheme 9.

Many attempts have been made to improve the selectivity of the Wittig reaction forming the upper chain.

Researchers of Schering (J. Westermann, M. Harre, K. Nickish, *Tetrahedron Letters*, 1992, 33, 8055-8056) investigated how the protecting groups of the bicyclic ketone, already containing the lower chain, and the reaction conditions of the Wittig reaction influenced the selectivity of the reaction.

Scheme 6.

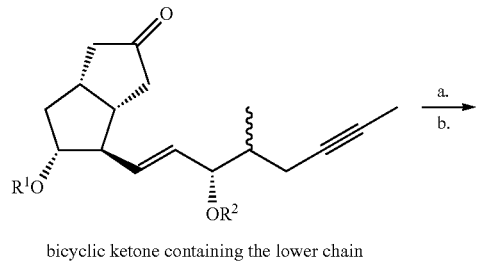

bicyclic ketone containing the lower chain

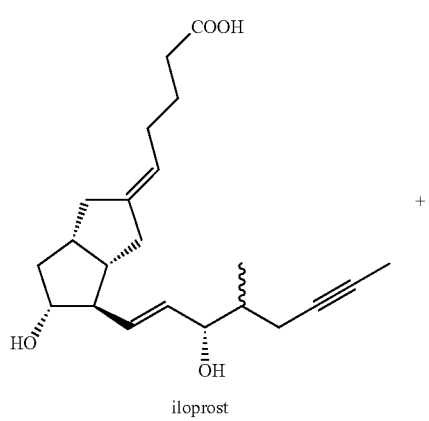

iloprost

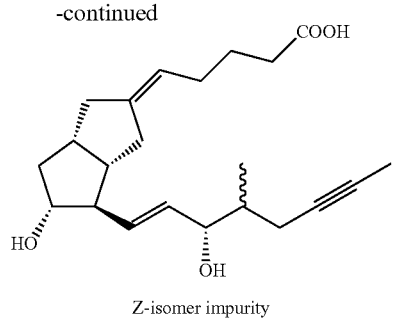

Z-isomer impurity a. Wittig reaction; 4-carboxybutyltriphenylphosphonium bromide/potassium-tert-butylate
b. deprotection, if R¹ and/or R² is not hydrogen Based on the experiments they stated that the worst isomeric ratio (E:Z=60:40) was obtained by use of THP protecting group ($R^1=R^2$=THP) and DMSO-THF solvent mixture.

The best isomeric ratio (E:Z=90:10) was achieved when the bicyclic ketone did not contain protecting group ($R^1=R^2$=H) and dimethoxyethane was chosen as solvent. H-J. Gais and his co-workers (*J. Am. Chem. Soc.*, 2005, 127, 17910-17920) repeated that reaction starting from Corey lactone which contained the chiral lower chain of iloprost, but they obtained a much less favourable isomeric ratio (E:Z=62:38).

Surveying the literature data, the hitherto known most selective method to construct the upper chain was worked out by H-J. Gais and his co-workers (G. J. Kramp, M. Kim, H-J. Gais, C. Vermeeren, *J. Am. Chem. Soc.*, 2005, 127, 17910-17920; H-J. Gais, G. J. Kramp, D. Wolters, L. R. Reddy, *Chem. Eur. J.*, 2006, 12, 5610-5617). The method was worked out for the synthesis of iloprost containing chiral lower chain.

The upper chain was constructed in two steps. The first step, assuring the selectivity, was carried out with chiral phosphonate. The lithium salt of the chiral phosphonate was reacted at (-)78-(-)62° C. with the protected bicyclic ketone corresponding to iloprost, but containing chiral lower chain. The chiral HWE reaction was carried out starting from 300 mg of bicyclic ketone. In the reaction only 2% of Z-isomer was formed. The ester group was reduced to the alcohol with diisobutylaluminum hydride (DIBAL-H), the alcohol was protected with acetyl group. The upper chain, with the appropriate number of carbon atoms, was built by treating the acetyl derivative with cuprate reagent protected with tert-butyldimethylsilyl (TBDMS) group. The protecting group of the primary alcohol was removed by mild desilylation (by treatment with neutral aluminum oxide in hexane), the primary alcohol was oxidized to the aldehyde with DMSO-pyridine reagent. The aldehyde was oxidized to the acid with silver nitrate, to obtain after removal of the protecting groups, the (16S)-iloprost which contains chiral lower chain (Scheme 7).

Scheme 7.
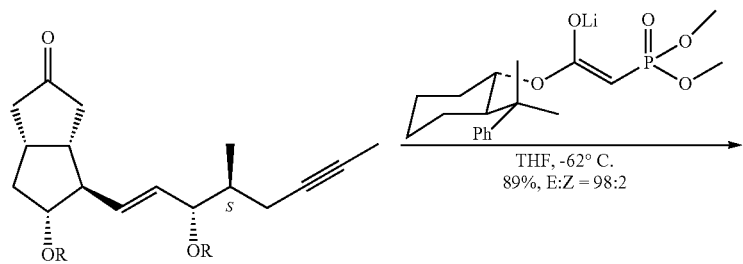
R = tert-butyldimethylsilyl
16(S)-iloprost intermediate with chiral lower chain
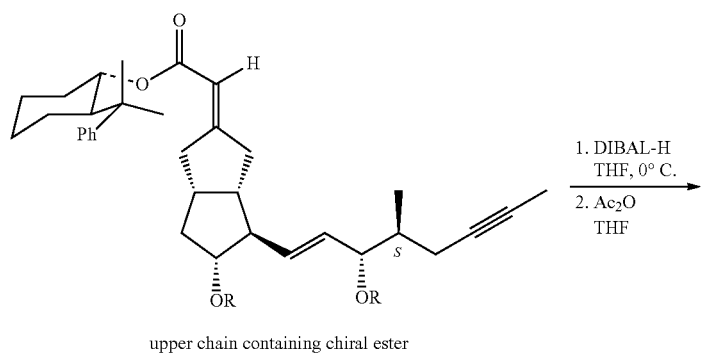
upper chain containing chiral ester
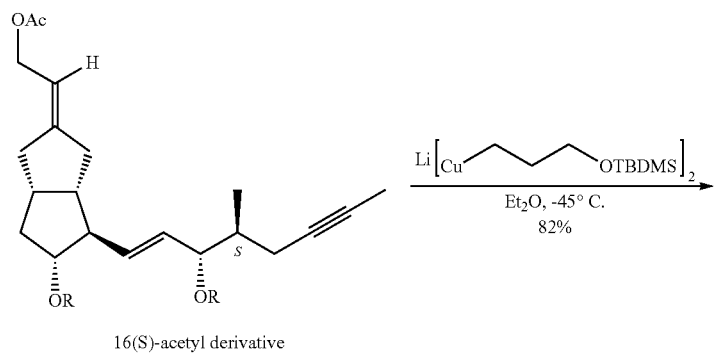
16(S)-acetyl derivative
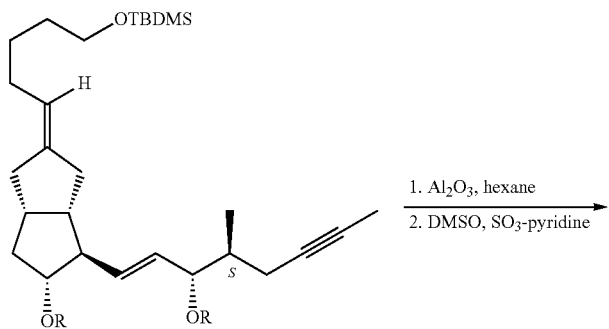
16(S)-TBDMS-iloprost-alcohol

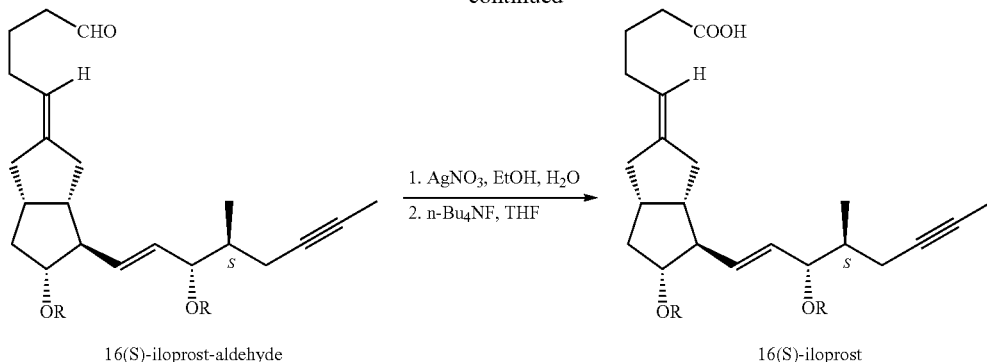

16(S)-iloprost-aldehyde → 16(S)-iloprost

1. AgNO₃, EtOH, H₂O
2. n-Bu₄NF, THF

The prepared amount of 16(S)-iloprost was 20 mg, its physical state was not characterized.

Advantage of the above process is that during the construction of the upper chain only 2% of Z-isomer impurity is formed. Disadvantages: it is hard to scale-up, it applies extreme reaction conditions and uses expensive reagents prepared in many-step syntheses.

In patent specification CN 107324986 preparation of the chiral (S)-TBDMS-enone is described, which is obtained by fractionated crystallisation of the racemic TBDMS-enone (FIG. 8).

From the chiral (S)-TBDMS-enone the 16(S)-iloprost may be prepared.

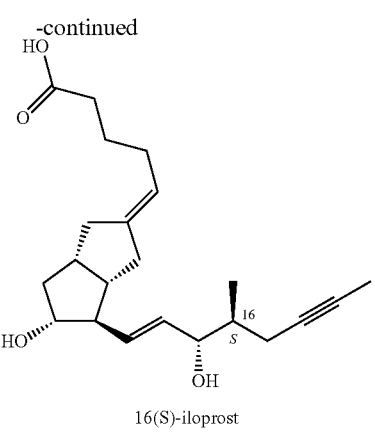

16(S)-iloprost

The process is the formal synthesis of 16(S)-iloprost. The patent application contains only the preparation of the chiral enone. As regards preparation and physical characterisation of the 16(S)-iloprost, neither a preparation example nor physical characteristics are given.

We aimed to work out an alternative synthesis for iloprost, which provides better yield than the hitherto known methods.

DESCRIPTION OF THE INVENTION

The Process According to the Invention Claimed in the Present Application is Outlined in Scheme 9.

Scheme 8.

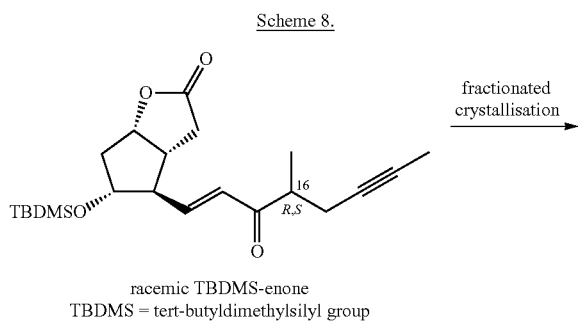

racemic TBDMS-enone
TBDMS = tert-butyldimethylsilyl group fractionated crystallisation 16(S)-TBDMS-enone Scheme 9.

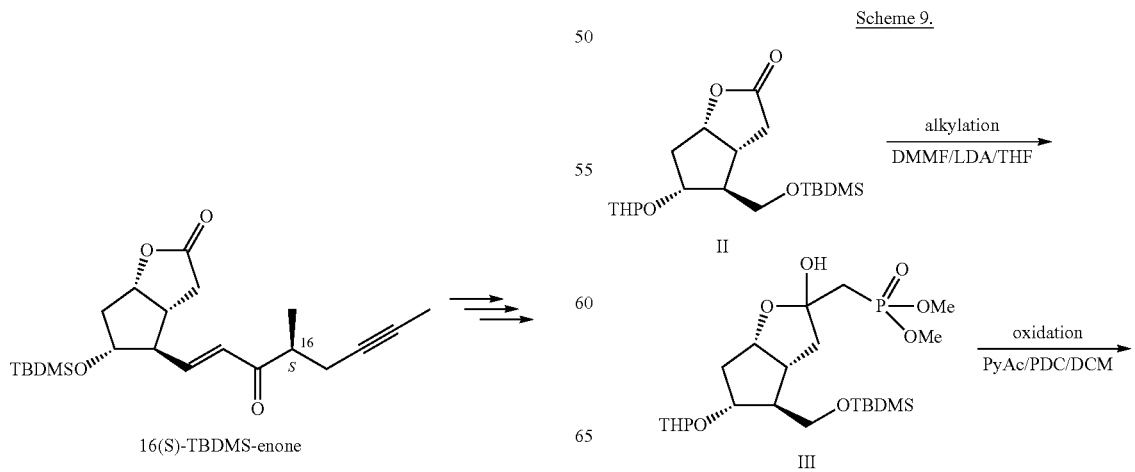

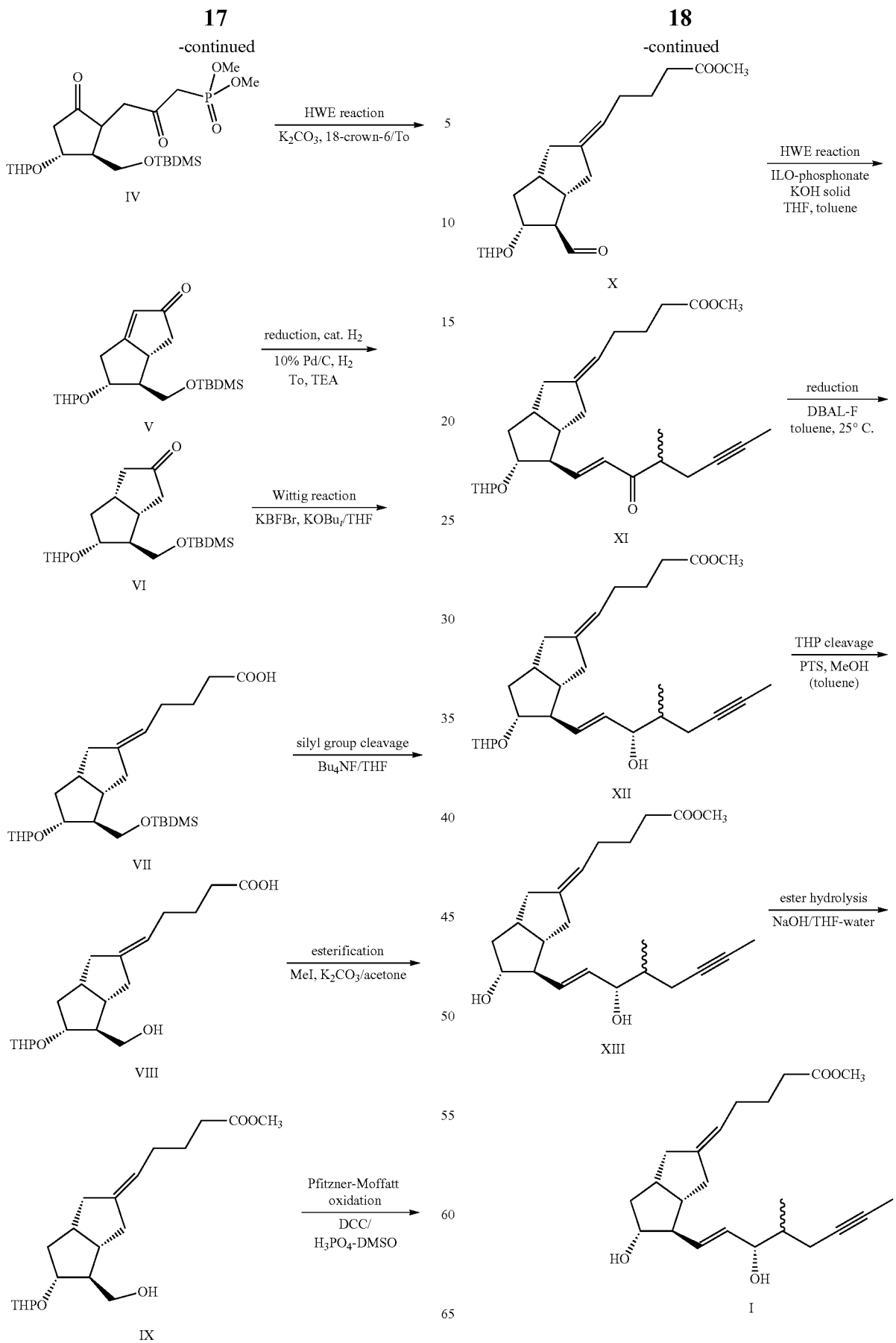

In the process according to the invention first the upper chain is built into the protected Corey lactone of formula II.

In the course of the preparation of compound III, to form the phosphonate, a strong base is required to deprotonate the dimethyl methylphosphonate. However, a strong base, as for example butyl lithium, applied in excess amount, will open the lactone ring (a latent carboxylic acid ester).

When a strong base, for example butyl lithium is used, the anion formed from the opened lactone ring will not be alkylated by the phosphonate and after work-up the starting material will be obtained back, depending on the reaction conditions in as much as 20% amount.

In the process according to the invention lithium diisopropylamide or lithium dialkylamides are applied which selectively deprotonate the methyl dimethylphosphonate, the lactone ring will not open (remains intact) thus the whole amount of compound II is alkylated by the phosphonate and the phosphonic acid ester is formed, the amount of the starting material after work-up remains below 2%.

In the case of the above compounds preferably lithium diisopropylamide is applied, as the diisopropylamine released from the reagent can be removed from the product.

During the preparation of the compound of formula IV

Scheme 10.

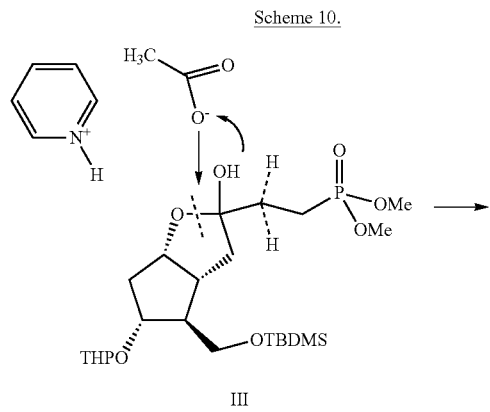

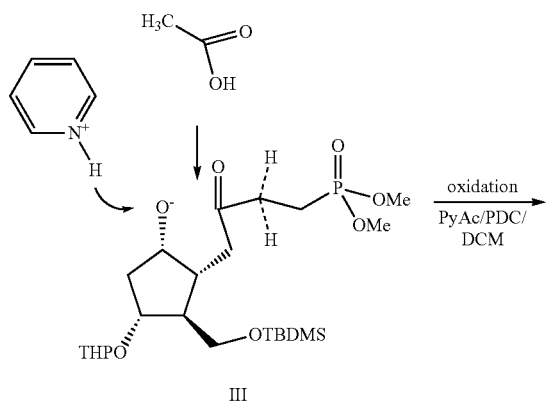

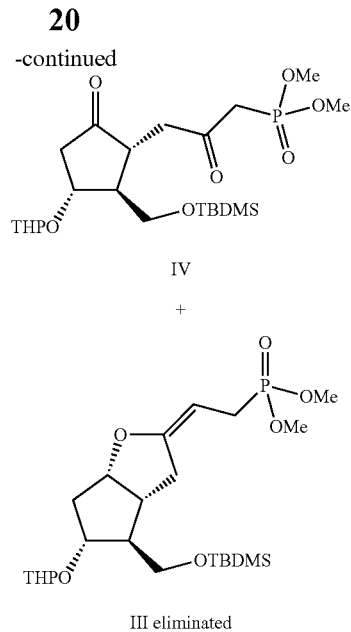

IV

+

III eliminated the lactol ring has to be opened (ketal cleavage) and the liberated secondary hydroxyl group has to be oxidized. The reaction clearly has to be performed in acidic medium, since under basic conditions an uncontrolled HWE reaction will start supplying the III eliminated side-product (Scheme 10) In the literature ("Synthesis of a carbaprostacyclin intermediate-6β-[(tert-butyldimethylsiloxy)methyl]-7-α-[(tetrahydropyran-2-yl)oxy]bicyclo[3.3.0]octan-3-one", Huaxue Xuebao, 1987, 45(7), 727-9; U.S. Pat. No. 4,420,632 A1, U.S. Pat. No. 9,831,213, GB 2070596, GB 2070596) simply the acidic conditions of Collins oxidant: $CrO_3$.pyridine, Jones reagent: $CrO_3$.aqueous sulfuric acid, PCC and PDC oxidations are utilized to open the ring, however, under strong acidic conditions the ketal affords via dehydration in about 20-30% the so-called eliminated compound III containing double bond.

In the process according to the invention the lactol ring is opened under very mild acidic conditions with pyridinium acetate, and following lactol opening, the liberated hydroxyl group is oxidized with PDC, which works under much milder conditions than PCC. The oxidation takes place slowly, but the amount of the so-called eliminated impurity and the decomposition products is much less, less than 5%.

For the preparation of the compound of formula V, similarly to the methods known from the literature, the process according to the invention also uses potassium carbonate in toluene medium, the catalyst of the intramolecular HWE (Horner-Wadsworth-Emmons) reaction is 18-crown-6 reagent. However, the known method has been developed by us. In this reaction step, two reactions, the intramolecular and the intermolecular HWE reaction are competing. Appropriate conditions, like high (preferably 3045-fold) dilution, high temperature (90-110° C.) and the applied addition method will favour the intramolecular HWE reaction. In our method of addition, to the refluxing solution of the reagents is added dropwise the solution of IV very slowly, therefore it immediately reacts intramolecularly. Since there is no excess of IV, there is no possibility to form dimers and participate in intermolecular Wittig reaction. The result: the ratio of dimers dropped from 15% to less than 3%. The yield increased from 35% to 50% (Scheme 11)

Scheme 11.

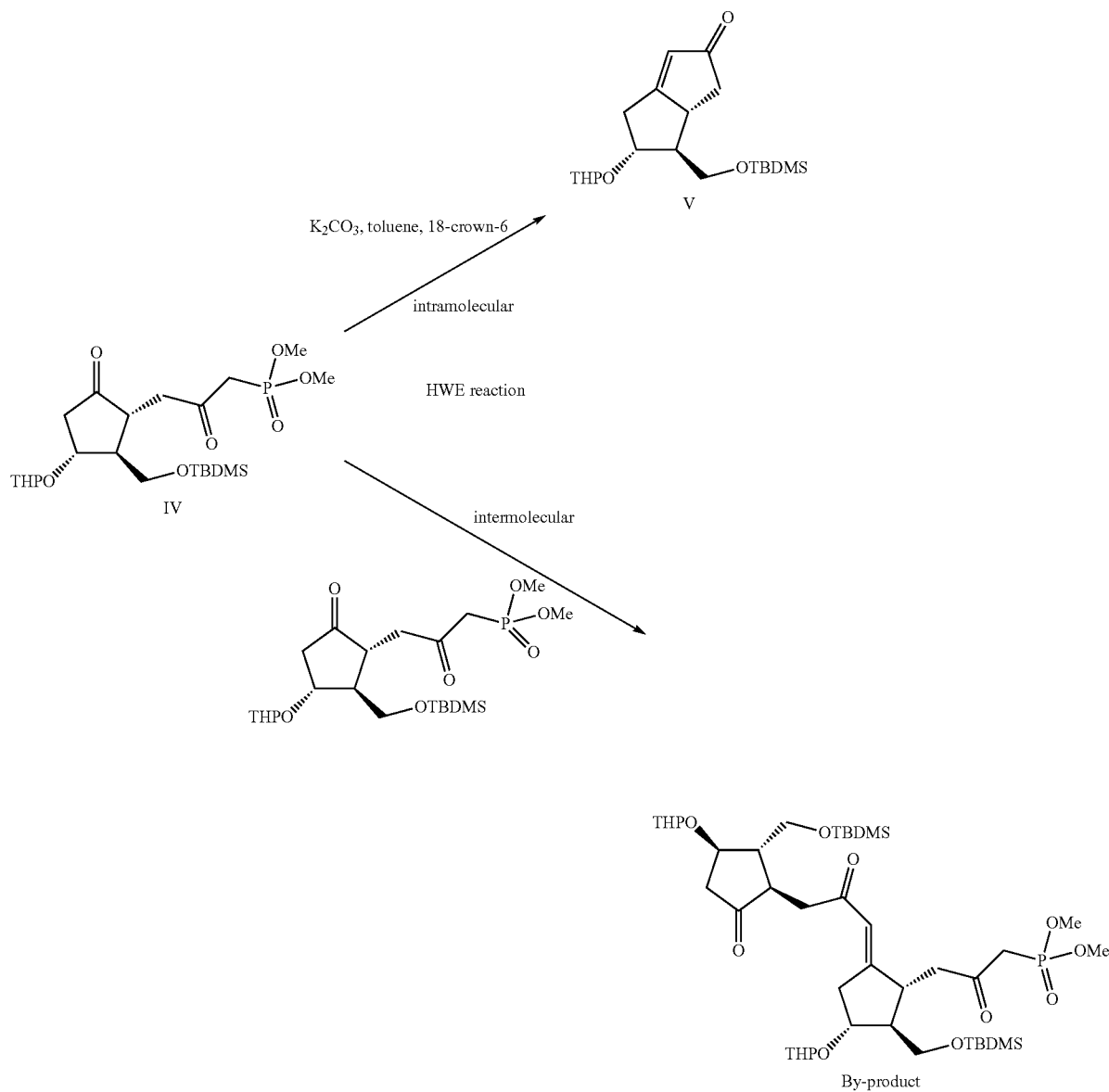

To prepare the compound of formula VI, reduction with palladium on charcoal, the method also used in the literature is applied, as solvent toluene is applied which contains triethylamine to protect the THP protecting groups. The intermediate is purified by chromatography. The reduction may also be carried out using Raney-Nickel catalyst.

In the process according to the invention the upper chain is constructed in the step where compound of formula VII is prepared by Wittig reaction. The TBDMS protecting group of the desired compound VII and that of the undesired isomeric impurity VIIz, obtained as by-product, is removed with tetrabutylammonium fluoride ($Bu_4NF$), the resulting compound VIII (E-isomer) and the Z-isomer impurity VIIIz are separated by gravitational chromatography. By high performance chromatographic purification the amount of the Z-isomer impurity may be decreased to 0.2-0.5% (optical purity, diastereomeric excess (de)=99.0-99.6%). For comparison: the purity reached in the stereoselective Wittig reaction, the method described in the literature, was only de=96%. (Scheme 12)

Scheme 12.

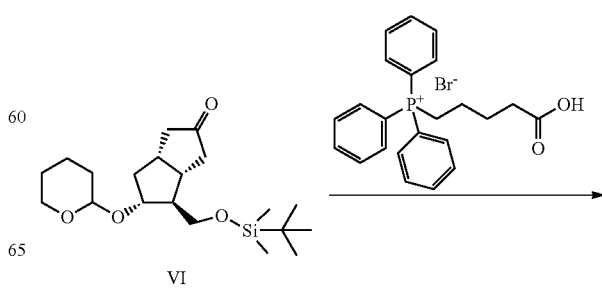

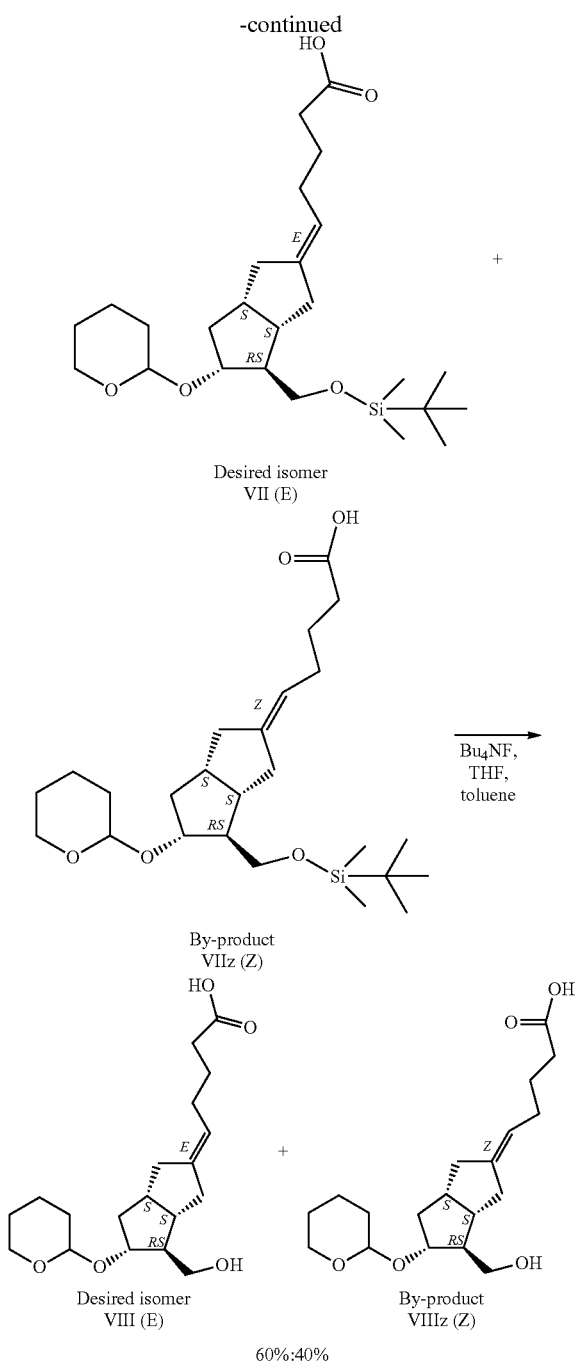

Desired isomer
VII (E)

By-product
VIIz (Z)

Bu₄NF,
THF,
toluene

Desired isomer
VIII (E)

By-product
VIIIz (Z)

60%:40%

In the process according to the invention the undesired Z-isomer (VIIIz) may be recycled into the synthesis. In our recycling method the undesired Z-isomer is isomerized in UV reactor, in toluene medium in the presence of sensibiliser (10 mol % of dimethyl disulfide) and from the mixture containing 10-30% of E-isomer we obtain a product with approx. 55% E-isomer content, which after chromatographic purification provides the E-isomer (VIII) in 41% yield, which is can be recycled into the purification process. The yield of intermediate VIII starting from intermediate VI is 65%. Comparing technical feasibility and expenses of our method with that of H-J. Gais and his co-workers, where in the HWE reaction chiral phosphonate is applied, we can state that the process according to the present invention is more economical, it does not require the expensive chiral phosphonate prepared in many steps.

The compound of formula VIII is esterified by known method, in acetone with methyl iodide in the presence of potassium carbonate providing the ester of formula IX.

To prepare the compound of formula X from compound IX three methods have been elaborated, Pfitzner-Moffatt oxidation with DMSO and phosphoric acid containing DCC or DIC, as well as Anelli oxidation (sodium hypochlorite, TEMPO catalyst). From the obtained compound of formula X the lower chain was built by HWE method.

When Pfitzner-Moffatt oxidation is applied, during the HWE reaction the phosphonate is preferably liberated one-pot. After the oxidation the compound of formula X is in toluene solution, to the solution a small amount of THF, then the ILO-phosphonate and then solid KOH are added. The favourable effect of the KOH is that it does not dissolve in the reaction mixture, thus it solely reacts with the ILO-phosphonate and gives practically no reaction with the aldehyde X, therefore the amount of the impurity formed from the aldehyde is very low.

The advantage of the oxidation with TEMPO catalyst, as compared to the Pfitzner-Moffatt oxidations, is that it does not produce a high amount of carbamide derivative which is difficult to remove.

The compounds of formulae X and XI are new compounds.

In the method according to the invention the compounds of formula XI are reduced.

Four different reducing agents have been tried (Cerium (III)chloride/NaBH₄, catecholborane-CBS-oxazaborolidine catalyst, diisoborneol-oxy-diisopropyl aluminate, DIBAL-F). Effects of other parameters (e.g. temperature) were also investigated.

The most favourable reducing agent turned to be the DIBAL-F, this reagent was prepared by reacting diisobutylaluminum hydride with 2,6-di-tert-butyl-4-methylphenol.

The main impurity is the by-product of the reduction, 11-THP-15-epi-iloprost methyl ester. (Scheme 13)

Scheme 13.

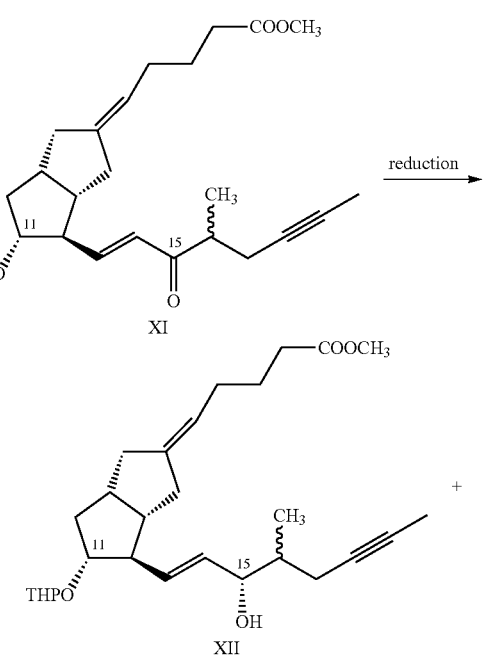

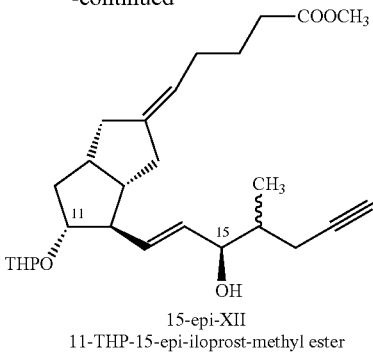

15-epi-XII
11-THP-15-epi-iloprost-methyl ester

The ratio of the product and the 15-epimer in the reduction was 75:25 by use of DIBAL-F reducing agent (in the first experiments, using cerium chloride/sodium borohydride reagents this isomeric ratio was 60:40).

After decomposition of the reducing agent and removal of the water-soluble by-products, the THP-group is cleaved with methanol and para-toluenesulfonic acid. In a preferred method the toluene solution is not worked-up, but the protecting group is removed without isolation of the compound of formula XII.

The compound of formula XII is new.

The compounds of formula XIII can be purified by chromatography. During normal phase gravitational chromatography (n-hexane:ethyl acetate) purification from the main by-product of the reduction, the epimer impurity, takes place in approx. 95%, in addition, the amount of some impurities which make the purification of iloprost difficult, are also decreased significantly.

The compound of formula XIII may also be purified by reverse phase- and preparative HPLC methods.

Both on C18 silica gel, and on polystyrol resin, by using eluents applicable on reverse phase, first of all acetonitrile:water or methanol:water eluents, compound XIII (iloprost methyl ester) can be purified excellently from related and other impurities. To remove related impurities the most powerful method is the purification of iloprost by preparative HPLC.

In the process according to the invention compound XIIIb, obtained as by-product, may be recycled into the synthesis, by oxidation it gives compound XIb which after protection of the 11-OH group with THP, provides the intermediate of formula XI. (Scheme 14)

Scheme 14.

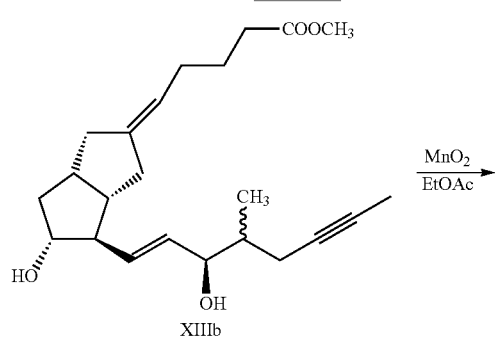

XIIIb

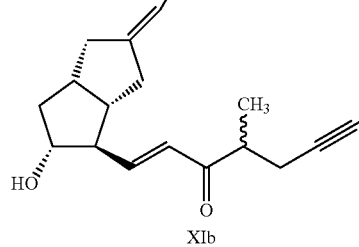

XIb

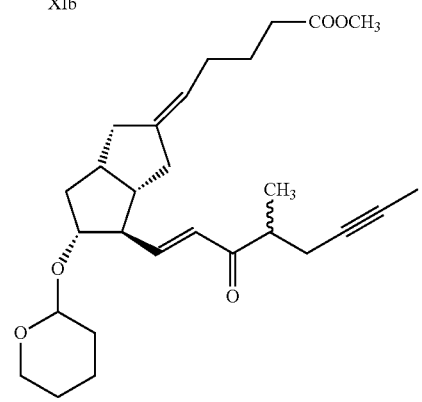

XI

Compound XIIIb is dissolved in ethyl acetate and filtered through activated manganese dioxide packing. The filtrate is repeatedly poured onto the packing and filtered. After the second filtration the product XIb is washed from the packing with ethyl acetate saturated with water, the liquid filtrate is combined with the washings and evaporated. The evaporated crude product is dried from water by adding and distilling off toluene.

Dihydropyrane and the catalyst, para-toluene sulfonic acid are added into the toluene solution to protect the 11-hydroxyl group with THP group. The reaction is terminated with triethylamine and the reaction mixture is evaporated. The obtained concentrate is recycled into the stereoselective reduction step to prepare XII.

By recycling the intermediate XI obtained from the by-product XIIIb, the yield of the selective reduction increases from 56% to 63% (XI-XIII).

Hydrolysis of the methyl ester of formula XIII provides iloprost, the hydrolysis is carried out in THF with aqueous NaOH solution under intensive agitation.

Iloprost, obtained at the end of the reaction still contains at a measurable level related impurities, 15-epi-iloprost and 15-oxo-iloprost and the by-products from the oxidation. Purification of iloprost is carried out by preparative HPLC. Two methods have been worked out, for the material not contaminated with 15-oxo-iloprost, an eluent containing acetonitrile:water, for iloprost contaminated with high level of 15-oxo-iloprost, an eluent containing alcohol:water is applied. During purification isomer Z of iloprost is also removed.

Our method is equally applicable for the preparation of 16(S)-iloprost and 16(R)-iloprost, if instead of the racemic ILO-phosphonate the HWE reaction is carried out using chiral (S)-ILO-phosphonate or chiral (R)-ILO-phosphonate.

The 16(S)-iloprost prepared in the enantioselective synthesis using chiral (5)-ILO-phosphonate, may also be isolated in crystalline form.

In accordance with the above, the invention relates to a process for the preparation of iloprost of formula I

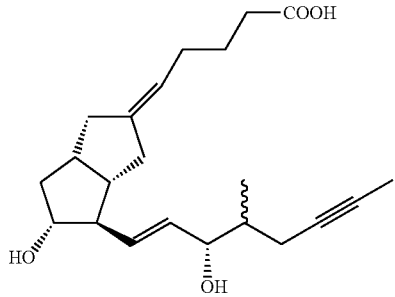

in a way that
a.) The Corey lactone of formula II

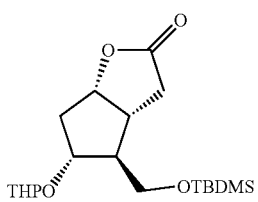

is selectively alkylated with dimethyl methylphosphonate in the presence of lithium dialkylamide,
b.) the ring of the resulting lactol of formula III

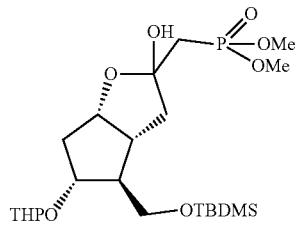

is opened with pyridinium acetate in mild acidic medium, then the obtained secondary hydroxyl group is then oxidized with pyridinium dichromate,
c.) the resulting compound of formula IV

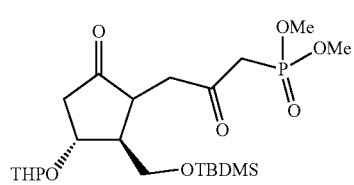

is reacted with potassium carbonate in the presence of 18-crown-6 reagent,
d.) the obtained compound of formula V

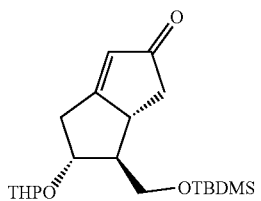

is reduced,
e.) the resulting compound of formula VI

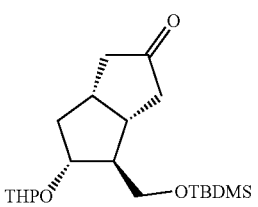

is reacted with carboxybutyltriphenylphosphonium bromide in the presence of potassium tertiary-butylate,
f.) the TBDMS protecting group of the obtained E- and Z-isomers of formula Vii

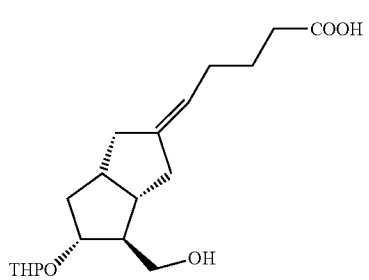

is removed, the isomers are separated by gravitational chromatography, if desired the Z-isomer (VIIIz) is isomerized into the E-isomer,
g.) the resulting compound of formula VIII is esterified,
h.) the obtained compound of formula IX

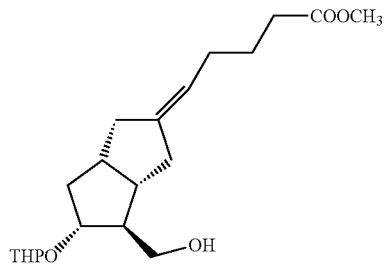

is oxidized,
i.) the resulting compound of formula X

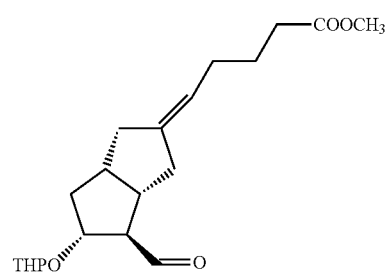

is transformed in HWE reaction in the presence of solid potassium hydroxide into the compound of formula XI,
j.) the oxo group of the thus obtained compound of formula XI

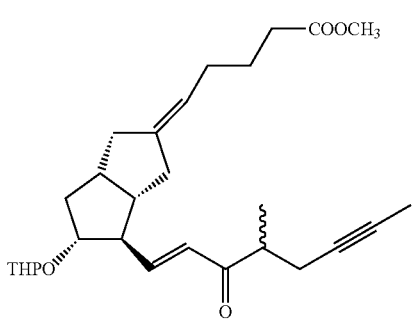

is reduced with DIBAL-F,
k.) the tetrahydropyranyl protecting group of the compound of formula XII

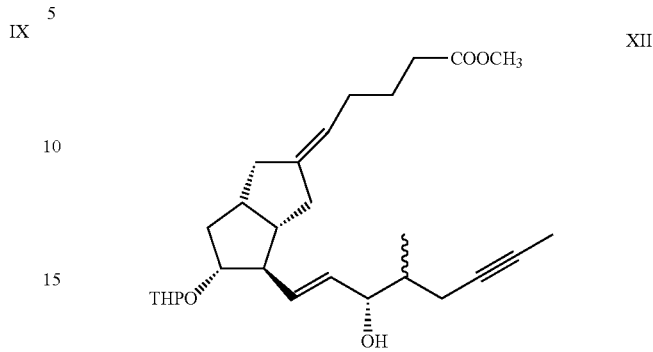

is removed and the compound is purified by gravitational column chromatography, if desired further purified by preparative HPLC,
l.) the ester group of the compound of formula XIII

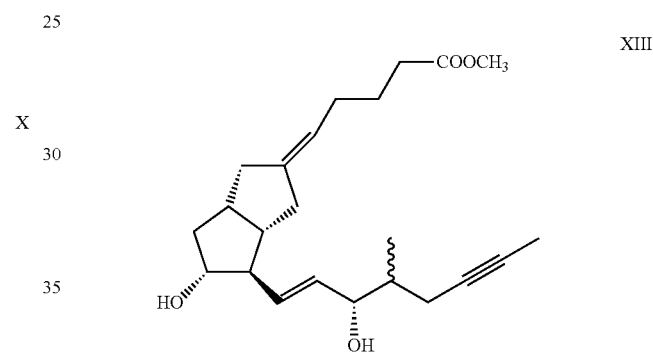

is removed and the obtained compound of formula I is purified.

In a preferred embodiment of the process according to the invention as lithium dialkylamide, lithium diisopropylamide or lithium dicyclohexylamide is applied. For preparation of the compound of formula V the HWE reaction is carried out in high dilution and at high temperature, preferably at 90-110° C., in a way that the solution of the compound of formula IV is added dropwise to the refluxing solution of the reagents.

Separation of the E- and Z-isomers of formula VIII is carried out using step-gradient mixtures of toluene:methyl tertiary-butyl ether as eluent.

Isomerisation of the Z-isomer is carried out by irradiation in the presence of dimethyl disulfide sensibiliser, cleavage of the silyl protecting group is effected with tetrabutylammonium fluoride trihydrate.

Oxidation of the compound of formula IX is carried out by Pfitzner-Moffatt oxidation with phosphoric acid-DMSO mixture containing DCC or DIC, or by Anelli oxidation (sodium hypochlorite, TEMPO catalyst).

In a preferred version of the process according to the invention compounds of formulae X and XII are not isolated.

In another preferred embodiment of the process according to the invention the 15R isomer of formula XIIIb, is separated by chromatography, and after oxidation then THP protection of the 11-OH group recycled into the synthesis.

The crude final product of formula I is purified by gravitational chromatography and/or preparative HPLC.

The compounds of formulae X, XI and XII are new compounds.

For iloprost final product the purity is the most important parameter, since products of different purity behave differently. From iloprost reaching a certain level of purity a solid-phase product can be prepared.

A further subject of our invention is preparation of the solid form of iloprost by dissolving the purified oily compound of formula I in the same amount of polar solvent as the mass of the oily product, adding such an amount of alkane to it that the solution turns opalescent, then solidifying the solution to a glassy mass at from (−)60° C. to (−)20° C. and removing the solvent in high vacuum.

Preferably the iloprost, already purified from its impurities, is subjected to a special treatment, it is dissolved in acetone, then pentane is added till the solution turns opalescent, the solution is then rapidly cooled to (−)60° C. where the oil fully precipitates from the acetone-pentane solution and the obtained precipitate solidifies, turns into a translucent, glassy, amorphous solid. After solidification iloprost is kept at (−)20° C., during this period, in the acetone-pentane medium the glassy solid transforms into a white, lumpy solid material. During solidification the solvent is several time removed by decantation and n-pentane is added to mixture in order to decrease the acetone content.

After the last decantation the solvents are removed from the suspension in high vacuum at (−)20° C., wherein the product transforms into a solid powder.

A: Crude Iloprost (Available Purity: 93%)

Iloprost methyl ester is dissolved in THF and hydrolysed with 1M NaOH solution into the acid. After hydrolysis, iloprost is in the aqueous alkaline phase in solution, in the form of its sodium salt. The mixture is extracted with methyl tertiary-butyl ether in order to decrease the amount of apolar impurities, then iloprost is liberated from its sodium salt with sodium hydrogen sulfate and extracted from the aqueous solution with methyl tertiary-butyl ether. After drying of the organic phase and evaporation, the crude iloprost is obtained in the form of an oil, which cannot be solidified, turn into its solid form, because of the high level of impurities. Purity of the obtained crude iloprost: 93% (oil).

For purification of the crude iloprost, obtained in the process according to the invention, we developed several methods:

| | Purification method | Appearance | Quality | Sum of impurities Related | Non-identified |
|---|---|---|---|---|---|
| B | 1. gravitational chromatography 2. solidification | oil | ≥95.0% | ≤3.5% | ≤2.5% |
| C | 1. preparative chromatography 2. filtration on silica gel 3. solidification | solid powder | ≥98.0% | ≤1.6% | ≤1.0% |
| D | 1. gravitational chromatography 2. preparative chromatography 3. filtration on silica gel 4. solidification | solid powder (crystal) | ≥98.5% | ≤1.6% | ≤0.5% |

B: Purification of Crude Iloprost by Gravitational Chromatography and Solidification (Achieved Purity: 95.0%)

Crude iloprost is purified by gravitational chromatography using step-gradient eluent mixtures and irregular silica gel of particle size 0.063-0.2 mm and pore size 60 Angström as packing. The material is dissolved in acetone, then such an amount of alkane is added to it that it turns opalescent. The solution is poured on the column, rinsed with the eluent and eluted. The eluents are mixtures of alkane:acetone, alkane:methyl ethyl ketone, alkane:ethyl acetate or alkane:isopropanol, where the alkane is n-pentane, n-hexane, cyclohexane, or heptane.

The main product of the gravitational chromatography, after evaporation of the solvents, has a purity higher than 95.0%, this product is already suitable for the preparation of solid iloprost by applying the techniques described below.

Iloprost oil, purified by gravitational chromatography, is dissolved in the same amount of acetone (or ethyl acetate or methyl ethyl ketone or isopropanol) as the mass of the oil, to the solution such an amount of normal pentane (or hexane, or cyclohexane or heptane) is added that it turns opalescent, the solution is then stored at (−)60° C., without agitation. After 6 hours the solution solidifies in the form of a glassy product. This glassy, solidified material is then stored at (−)20° C. for at least 16 hours, wherein it transforms into a white, lumpy solid form. The main part of the solvent is removed by decantation. At the end of the solidification the remaining solvent is removed in high vacuum at from (−)10° C. to (−)30° C.

The obtained purified iloprost is a white powder with a purity of 95.0%.

C: Purification of Crude Iloprost by Preparative HPLC, Followed by Filtration on Silica Gel and Solidification (Achieved Purity: 98.0%)

The crude iloprost is directly purified by preparative HPLC method. The material is dissolved in the same amount of acetonitrile as its mass, then water is added to it. The solution is filtered through a reverse phase pre-column made of C18 silica gel of particle size 10 micron and pore size 120 Angström. Purification of the filtered stock-solution is performed by high pressure preparative liquid chromatography, in reverse phase, using C8 or C18 packing or polystyrol resin packing and water-organic solvent mixtures as eluents. The organic solvent component of the eluent is acetonitrile, methanol, ethanol or isopropanol.

The combined main fraction of the chromatography is concentrated in vacuum at 40° C., the concentrated solution is extracted with methyl tertiary-butyl ether, the combined organic phase is washed with saturated salt solution, dried over sodium sulfate and concentrated in vacuum at 30° C.

To the concentrated solution first acetone, then carefully, until it turns opalescent, n-pentane is added. The solution thus obtained is then further purified by normal phase chromatography using 0.063-0.2 mm particle size and 60 Angström pore size irregular silica gel bed, and step-gradient mixtures of n-pentane:acetone as eluent. The main fraction is evaporated in high vacuum (0.1 mbar) at 30° C. The iloprost oil, filtered through silica gel, is transformed into the solid product as described under method B.

Iloprost, purified by the above method, is a white powder with a purity of 98.0%.

D: Purification of Crude Iloprost by Gravitational and Preparative HPLC, Followed by Filtration on Silica Gel and Solidification Crude iloprost is purified by gravitational chromatography as described in method B. The obtained iloprost oil is further purified by preparative HPLC method as described in method C. To the obtained concentrated solution acetone, and then carefully, until it turns slightly opalescent, n-pentane is added. The resulting solution is then further purified by normal phase chromatography on a bed made of 0.063-0.2 mm particle size and 60 Ångström pore size irregular silica gel, using step-gradient mixtures of n-pentane:acetone as eluent. The main fraction is evaporated in high vacuum at 30° C. The resulting iloprost oil filtered through silica gel is then transformed into the solid product as described under method B.

Iloprost, purified by the above method, is a white crystal with a purity of 98.5%.

Of the diastereomers separated by preparative HPLC, the 16(S)-iloprost may be crystallized. Preferably by dissolution in acetone and precipitation with pentane, it separates in crystalline form.

The further subject of the invention, the 16(S)-iloprost in crystalline form is novel.

In agreement with the above, by the process according to the invention, the followings may be prepared:

16(S)-iloprost isomer in crystalline phase.

Iloprost of oily or solid powder phase, with a purity of at least 98.5%, wherein the total amount of related impurities is not more than 1.6%, the total amount of non-identified impurities is not more than 0.5% and the amount of non-identified impurities, each is not more than 0.1%.

Iloprost of oily or solid powder phase with a purity of at least 98.5% meets the following quality requirements:

| Related impurities (HPLC) | |
|---|---|
| Iloprost Z-isomers, total | ≤0.60% |
| other impurities, total of which | ≤1.0% |
| 15-epi-Iloprost | ≤0.10% |
| 15-oxo-Iloprost | ≤0.20% |
| Iloprost methyl ester | ≤0.20% |
| Iloprost ethyl ester | ≤0.05% |
| Iloprost dimer 1 | ≤0.10% |
| Iloprost dimer 2 | ≤0.10% |
| non-identified impurities, each | ≤0.10% |

Iboprost of oily or solid powder phase with a purity of at least 98.0%, wherein the total amount of related impurities is not more than 1.6%, the total amount of non-identified impurities is not more than 1.0% and the amount of non-identified impurities, each is not more than 0.1%.

Iloprost of oily or solid powder phase with a purity of at least 98.0% satisfies the following quality requirements:

| Related impurities (HPLC) | |
|---|---|
| Iloprost Z-isomers, total | ≤0.60% |
| other impurities total of which | ≤1.0% |
| 15-epi-Iloprost | ≤0.20% |
| 15-oxo-Iloprost | ≤0.20% |
| Iloprost methyl ester | ≤0.10% |
| Iloprost ethyl ester | ≤0.10% |
| Iloprost dimer 1 | ≤0.20% |
| Iloprost dimer 2 | ≤0.20% |
| non-identified impurities, each | ≤0.10% |

Iloprost of oily or solid powder phase with a purity of at least 95.0%, wherein the total amount of related impurities is not more than 3.5% and the total amount of non-identified impurities is not more than 2.5%.

The 16(S)-iloprost in crystalline phase may also be prepared by the demonstrated chemical route, m.) if the aldehyde of formula X is transformed into the compound of formula (S)-XI by reaction with (S)-ILO-phosphonate in the presence of solid potassium hydroxide,

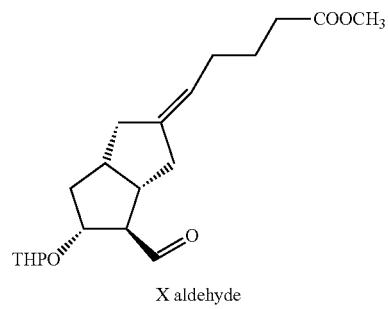

X aldehyde

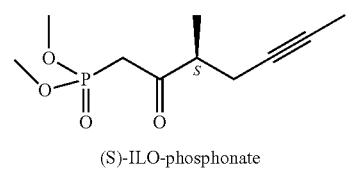

(S)-ILO-phosphonate n.) the oxo group of the obtained compound of formula (S)-XI

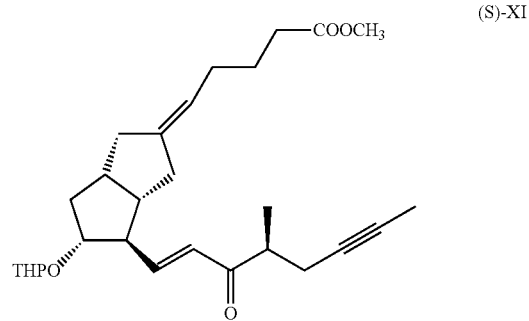

(S)-XI is reduced with DIBAL-F, o.) the tetrahydropyranyl protecting group of the compound of formula (S)-XII

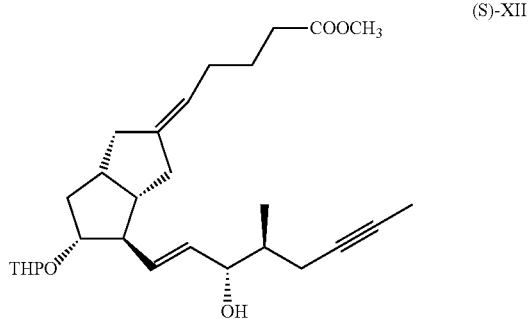

(S)-XII is cleaved and the compound is purified by chromatography,
p.) the ester group of the resulting compound of formula (S)-XIII

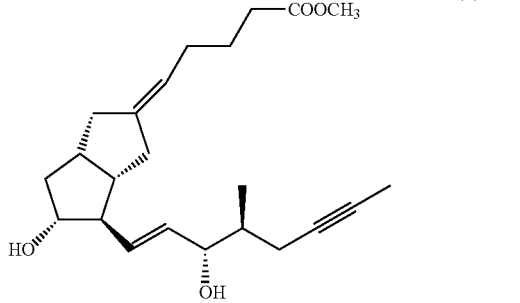

is removed and the obtained compound of formula (S)-I is purified.
q.) If the aldehyde of formula X is transformed into the compound of formula (R)-XI by reaction with (R)-ILO-phosphonate in the presence of solid potassium hydroxide,

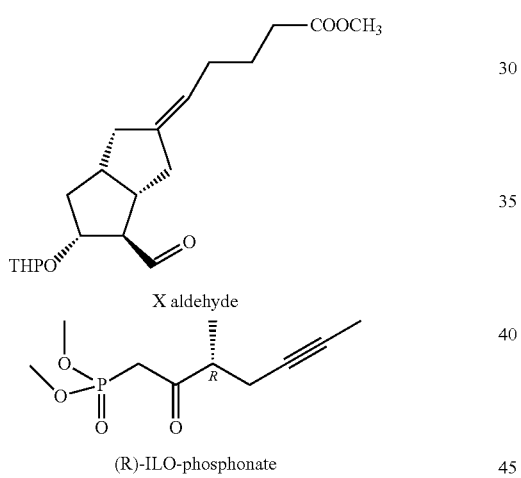

r.) the oxo group of the obtained compound of formula (R)-XI

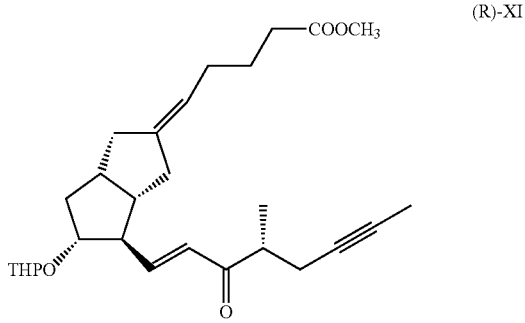

is reduced with DIBAL-F,
s.) the tetrahydropyranyl protecting group of the compound of formula (R)-XII

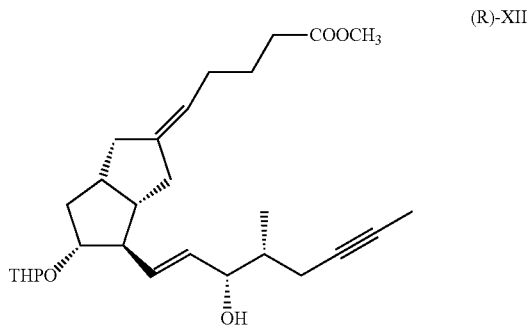

is cleaved and the compound is purified by chromatography,
t.) the ester group of the resulting compound of formula (R)-XIII is removed

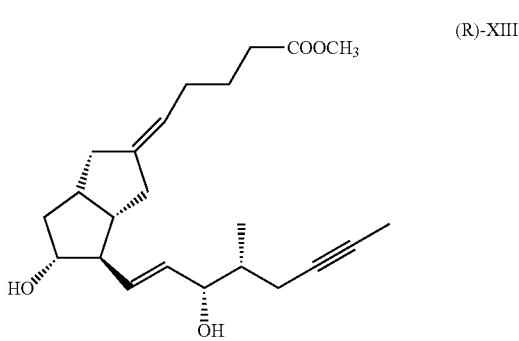

and the obtained compound of formula (R)-I is purified, then the 16-(R)-iloprost isomer may also be prepared.

BRIEF DESCRIPTION OF DRAWINGS/FIGURES

Figure 2:
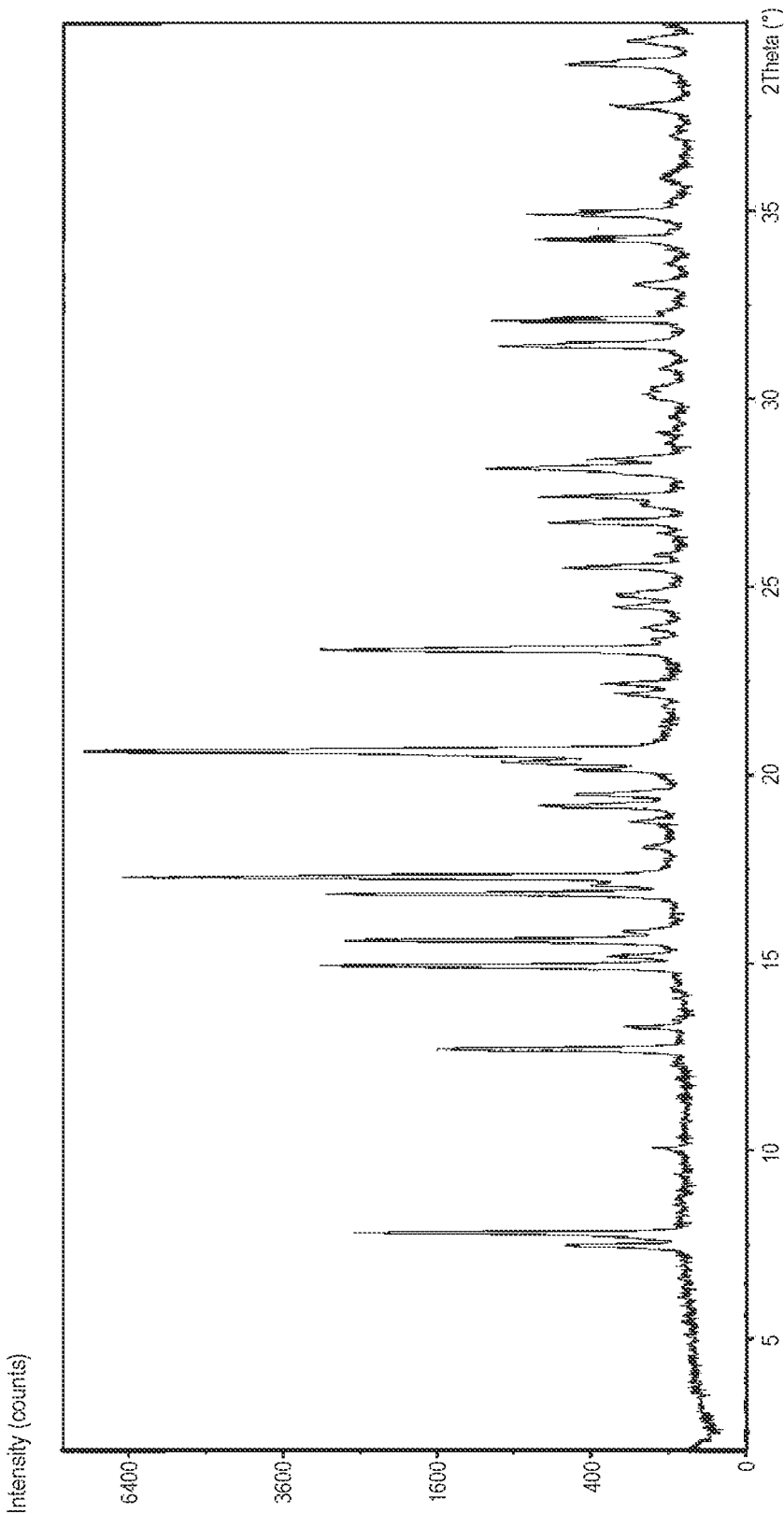
Figure 3:
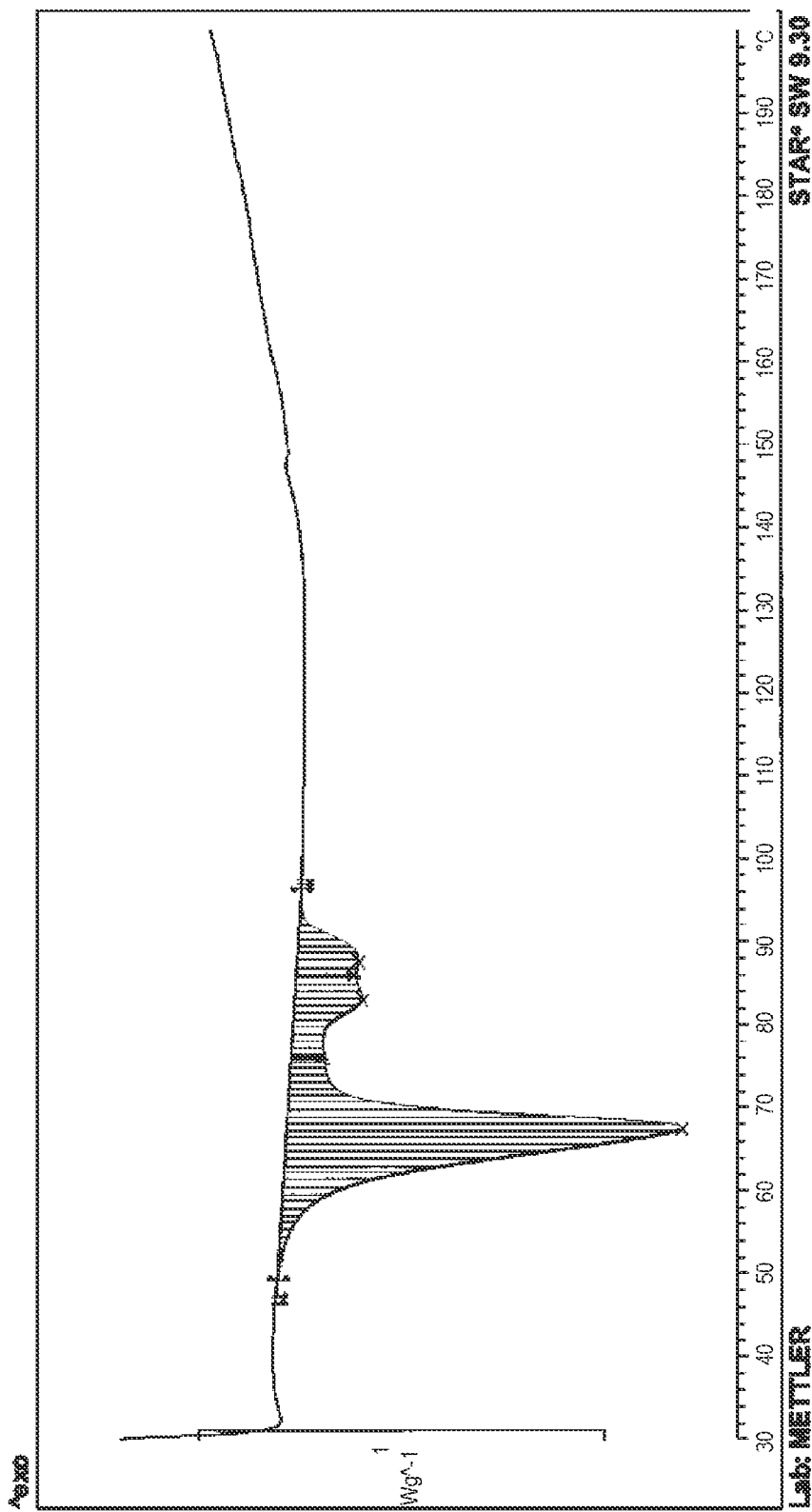
Figure 4:
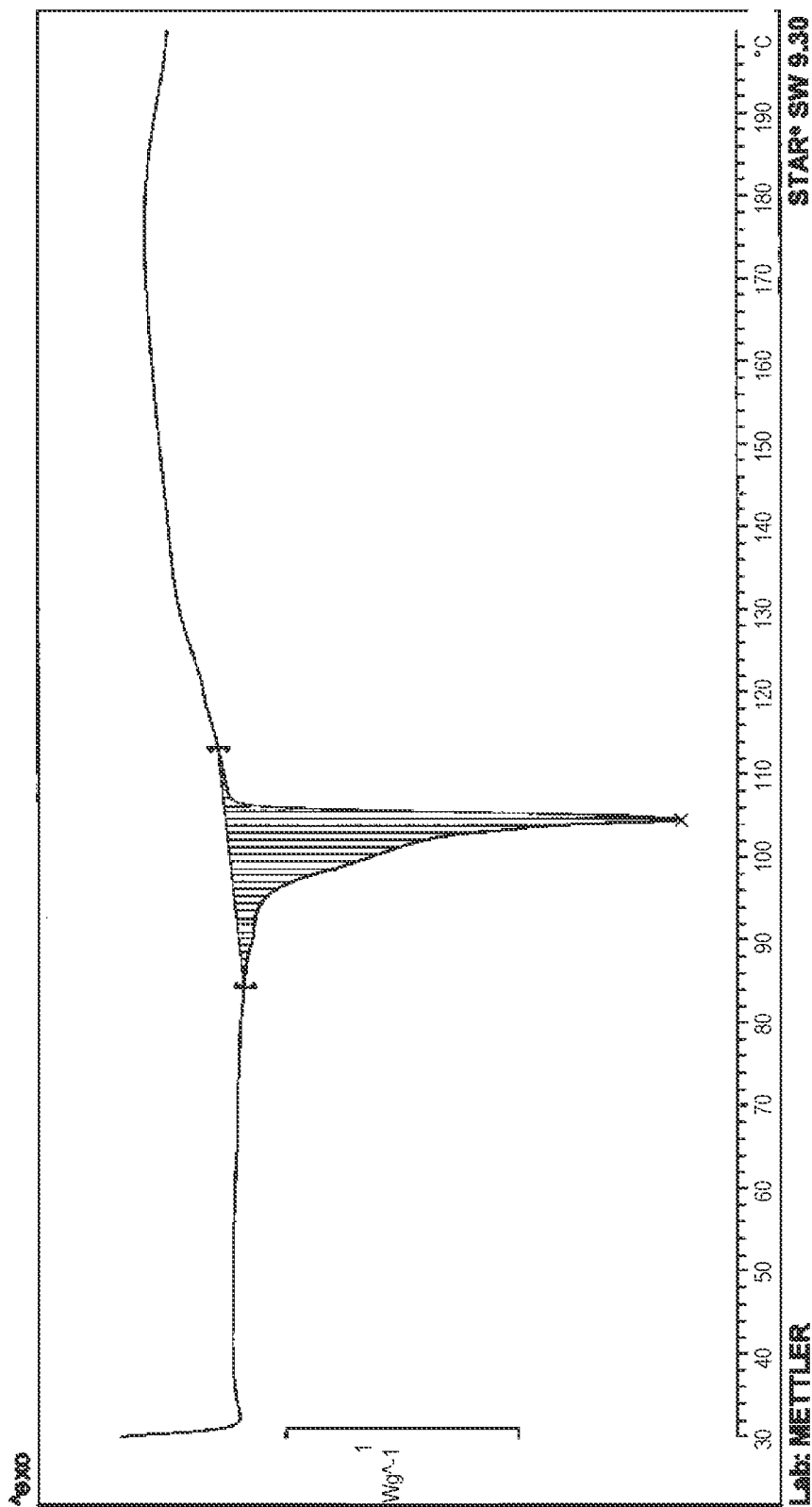
Figure 5:
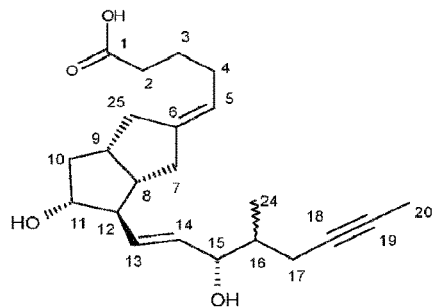
Figure 6:
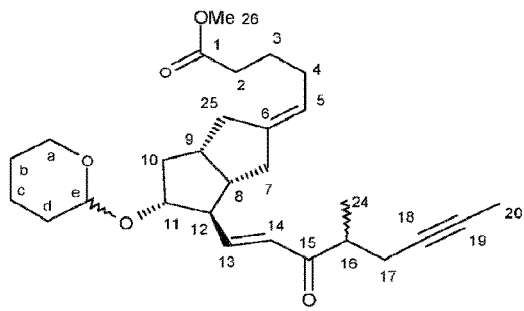

FIG. 1: XRPD pattern of iloprost (example 1m.)
FIG. 2: XRPD pattern of 16-(S)-iloprost (example 1n.)
FIG. 3: DSC curve of iloprost (peak: 67.58° C., example 1m.)
FIG. 4: DSC curve of 16-(S)-iloprost (peak: 104.62° C., example 1n.)
FIG. 5: $^{13}$C and $^{1}$H NMR data of iloprost acquired at 500 MHz in DMSO (example 1m.)
FIG. 6: $^{13}$C and $^{1}$H NMR data of compound of formula XI acquired at 500 MHz in DMSO (example 1h.)
FIG. 7: $^{13}$C and $^{1}$H NMR data of compound of formula (S)-XI acquired at 500 MHz in DMSO (example 1o.)
FIG. 8: $^{13}$C and $^{1}$H NMR data of compound of formula (S)-XII acquired at 500 MHz in DMSO (example 1p.)
FIG. 9: $^{13}$C and $^{1}$H NMR data of 16-(S)-iloprost acquired at 500 MHz in DMSO (example 1n.)

EXAMPLES

The subject of the invention is detailed in the examples, without limiting the claims to the variants of methods described in the examples.
Conditions of the measurements applied in the processes according to the invention:
X-Ray Diffractions:
Starting position [°2Theta]: 2.0074

End position [°2Theta]: 39.9854
Temperature of measurement [° C.]: 25.00
Material of the anode: Cu
K-Alpha1 [L]: 1.54060
K-Alpha2 [L]: 1.54443
DSC:
Instrument: METTLER TOLEDO DSC1 STARe System, Stare basic V9.30
Method: Starting temperature: 30° C.
  Final temperature: 200° C.
  Heating rate: 5° C./min
  Amount: 5-9 mg, perforated aluminum crucible (40 μl)
NMR:
Instrument: Bruker Avance III 500 MHz
Solvent: DMSO 1a/Preparation of the [[4-[[[(1,1-dimethylethyl)dimethylsilyl]oxy]methyl]hexahydro-2-hydroxy-5-[(tetrahydro-2H-pyran-2-yl)oxy]-2H-cyclopenta[b]furan-2-yl]methyl]phosphonic acid dimethyl ester (III)

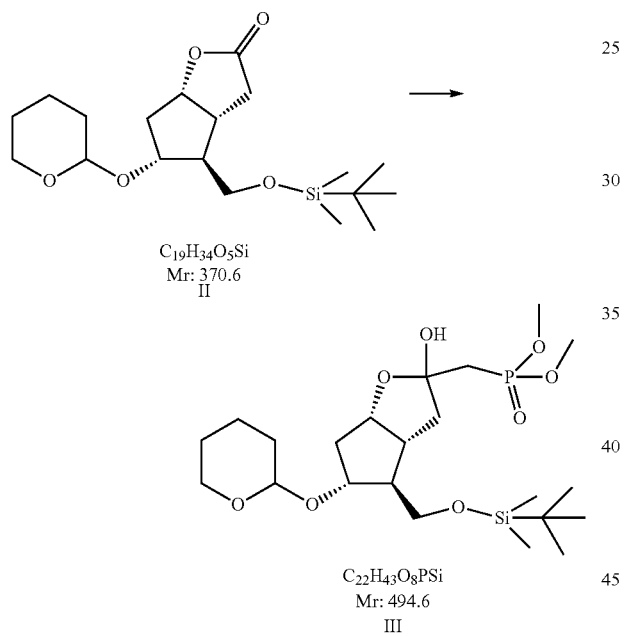

In 50 L of anhydrous tetrahydrofuran, under inert atmosphere, 4.2 L of dimethyl methylphosphonate is dissolved and the reaction mixture is cooled to (−)75° C. While keeping the prescribed temperature, 22.5 L of n-butyl lithium in 1.6M hexane solution, then 7.5 kg of II in 15 L of anhydrous tetrahydrofuran solution are added. At the end of the reaction the reaction mixture is quenched with 1M sodium hydrogen sulfate. The quenched reaction mixture is extracted with toluene, the organic phase is washed with sodium hydrogen carbonate solution containing sodium chloride and the toluene solution is evaporated in vacuum at 50° C.

Yield: 9.6 kg (96%), oil.

1a/B

LDA solution is prepared: into 28.7 kg of tetrahydrofuran 5.8 kg of diisopropylamine is added, the solution is cooled to 0±5° C., then in a period of 1 hour, under nitrogen flow, continuous agitation and cooling 21 kg of 1.6M butyl lithium solution is added thereto while keeping the temperature at 0±5° C. After the addition cooling is stopped and the mixture is agitated at 5±10° C. for 1 hour.

In a second apparatus, in 32.3 kg of tetrahydrofuran 7.5 kg of II is dissolved, to the solution 4.2 L of dimethyl methylphosphonate is added, the mixture is cooled to (−)5±5° C. under nitrogen flow and agitation, then the previously prepared LDA solution is added to the mixture while keeping the temperature between (−)5° C. and (+5° C.

The reaction is followed by TLC. Expected reaction time: 60 minutes.

At the end of the reaction the mixture is transferred by suction onto 1M sodium hydrogen sulfate solution and toluene is added to it. The aqueous phase is extracted twice with toluene, the combined organic phase is washed sequentially with 15% sodium chloride solution and 1N sodium hydrogen carbonate solution. The organic phase is evaporated in vacuum.

Yield (corrected to dry material content): 9.6 kg (96%). Colorless oil.

1b. Preparation of [1R-(1α,2,3α)]-[3-[2-[[[(1,1-dimethylethyl)dimethylsilyl]oxy]methyl]-5-oxo-3-[(tetrahydro-2H-pyran-2-yl)oxy]cyclopentyl]-2-oxopropyl]phosphonic acid dimethyl ester (IV)

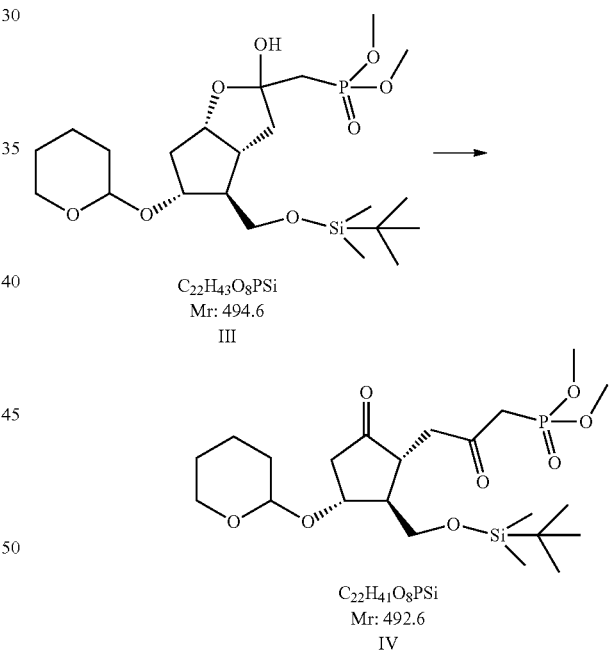

Preparation of the Pyridinium Acetate Reagent

To 170 kg of distilled dichloromethane 11.5 kg of pyridine is weighed and under agitation 6.9 kg of acetic acid is added. The mixture is cooled under agitation to 25±5° C.

Ketal Hydrolysis and Oxidation

To the pyridinium acetate solution 9.6 kg of III dissolved in 14 L of dichloromethane is added. The mixture is agitated under nitrogen atmosphere.

After 30 minutes of agitation 9.6 kg of pyridinium dichromate is added and the mixture is agitated at 25±5° C. till the prescribed conversion is reached. The reaction is followed by TLC. Expected reaction time: 24-48 hours. When the desired conversion is reached the reaction mixture is heated to 40±5° C., agitated for 30 minutes, cooled back to 25±5° C. and then toluene and perfil are added. The solid materials are removed by centrifugation. The filtrate which contains the product is washed with 2M sodium hydrogen sulfate solution, the phases are separated. The aqueous phase is extracted with toluene, the combined organic phase is washed sequentially with sodium hydrogen carbonate solution containing sodium chloride and 20% sodium chloride solution, dried over sodium sulfate and concentrated in vacuum at 50° C. to the defined volume. The concentrated residue is purified by chromatography using silica gel column and step-gradient mixtures of diisopropyl ether:acetone eluent.

Yield: 6.0 kg (62.8%), oil.

1c. Preparation of [5R-(5α,6β,6aα)]-6-[[[(1,1-dimethylethyl)dimethylsilyl]oxy]methyl]-4,5,6,6a-tetrahydro-5-[(tetrahydro-2H-pyran-2-yl)oxy]-2(1H)-pentalenone (V)

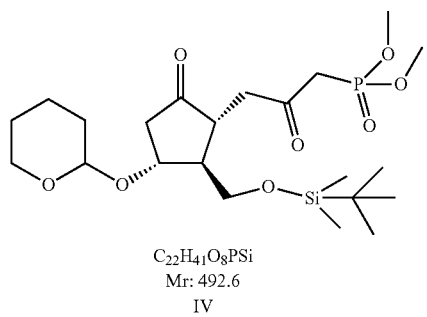

$C_{22}H_{41}O_8PSi$
Mr: 492.6
IV

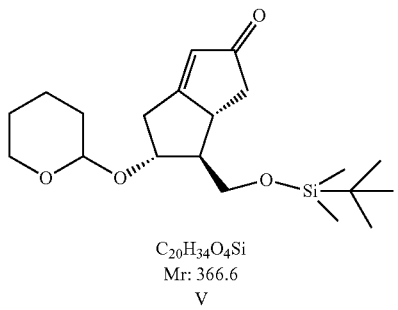

$C_{20}H_{34}O_4Si$
Mr: 366.6
V

To 50 L of anhydrous toluene under inert atmosphere 0.34 kg of 18-crown-6 and 3.4 kg of potassium carbonate are weighed. The reaction mixture is heated to 90° C. and the solution of 6 kg of IV in anhydrous toluene is added to it.

The reaction mixture is agitated while keeping the temperature. After reaching the desired conversion the mixture is cooled to room temperature, potassium carbonate is filtered off, the filtrate is concentrated in vacuum at 45° C.

Yield: 4.4 kg (98.5%), oil. The oily product may be used in the next step without purification.

If desired, the product may be purified by chromatography using gradient mixtures of hexane:diisopropyl ether, yield of the main fraction: 2.23 kg oil (50%).

1d. Preparation of [3aS-(3aα,4α,5β,6aα)]-4-[[[(1,1-dimethylethyl)dimethylsilyl]oxy]methyl]hexahydro-5-[(tetrahydro-2H-pyran-2-yl)oxy]-2(1H)-pentalenone (VI)

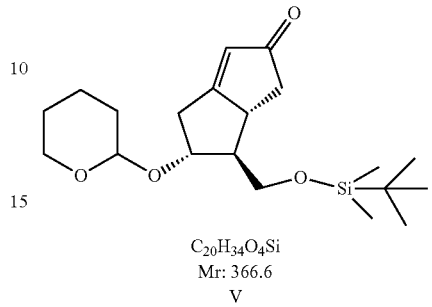

$C_{20}H_{34}O_4Si$
Mr: 366.6
V

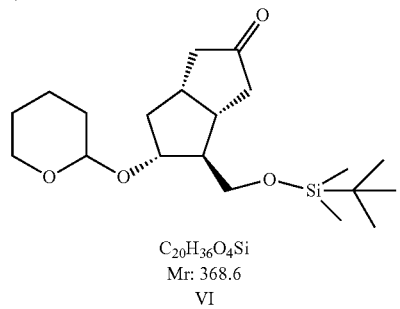

$C_{20}H_{36}O_4Si$
Mr: 368.6
VI

To 6.5 kg of V dissolved in 50 L of toluene, 100 ml of triethylamine is added and the mixture is hydrogenated at room temperature, under 3.5 bar pressure, using palladium on carbon catalyst containing 10% of palladium. At the end of the reaction the catalyst is filtered off, washed with toluene and the filtrate is concentrated in vacuum at 45° C. The concentrated residue is purified by chromatography on silica gel column using n-hexane:diisopropyl ether and diisopropyl ether:acetone mixtures as eluents. To the n-hexane:diisopropyl ether solvent mixture used for the preparation of the column, 0.03% amount by volume of triethylamine is added.

Yield: 1.5 kg (23%), oil.

1e. Preparation of [3aS-(2E,3aα,4α,5β,6aα)]-5-[4-[[[(1,1-dimethylethyl)dimethylsilyl]oxy]methyl] hexahydro-5-[(tetrahydro-2H-pyran-2-yl)oxy]-2 (1H)-pentalenylidene]pentanoic acid (VII)

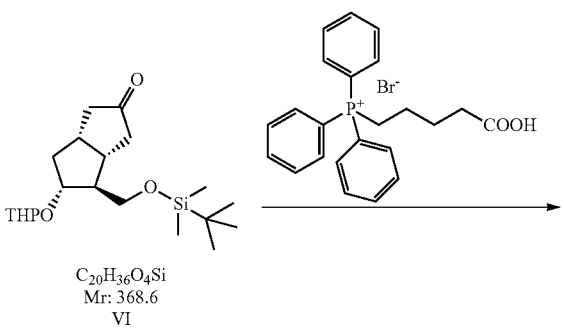

$C_{20}H_{36}O_4Si$
Mr: 368.6
VI

1f/A Preparation of [3aS-(2E,3aα,4α,5β,6aα)]-5-[hexahydro-4-(hydroxymethyl)-5-[(tetrahydro-2H-pyran-2-yl)oxy]-2(1H)-pentalenylidene]pentanoic acid (VIII)

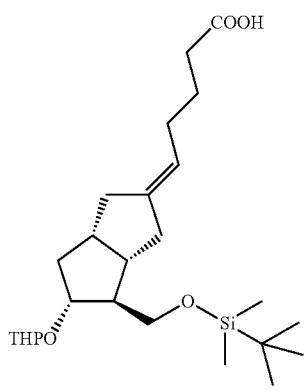

C₂₅H₄₄O₅Si
Mr: 452.7
VII

+

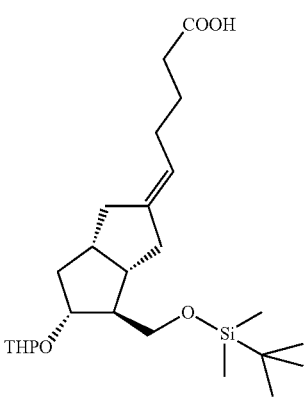

C₂₅H₄₄O₅Si
Mr: 452.7
VII

VIIz 7.0 kg of carboxybutyltriphenylphosphonium bromide is weighed into 35 L of anhydrous tetrahydrofuran, the reaction mixture is cooled to 5° C. and 3.8 kg of potassium tert-butylate is added. The mixture is agitated at room temperature for 15 minutes, then cooled to 5° C. and the solution of 1.7 kg of VI in 8 L of tetrahydrofuran is added. Agitation is continued while keeping the temperature until the desired conversion is reached, then water is added and the mixture is concentrated in vacuum at 45° C. The concentrated reaction mixture is cooled to 10° C., the precipitated solid material is filtered off, the liquid filtrate is diluted with water, washed with methyl ethyl ketone:n-hexane mixture. The pH of the aqueous phase is set to pH=7-7.5 with 1N sodium hydrogen sulfate solution. The aqueous phase is extracted with diisopropyl ether. The organic phase is washed with 20% sodium chloride solution and after addition of triethylamine it is evaporated in vacuum at 45° C.

Yield: 1.71 kg (82%, mixture of VII and VIIz), oil.

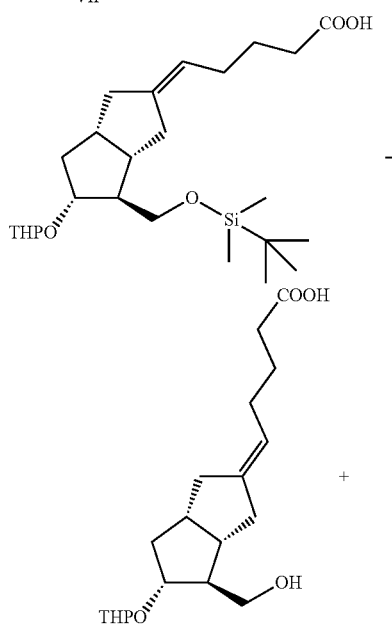

C₁₉H₃₀O₅
Mr: 338.4
VIII

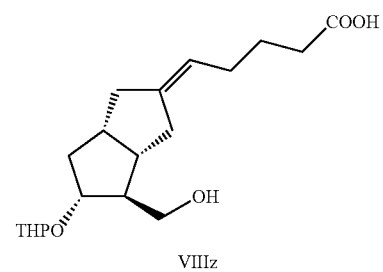

VIIIz 3 kg of tetrabutylammonium fluoride trihydrate is suspended in 10 L of toluene and dried from water by distilling off toluene. The anhydrous suspension is cooled to 20° C.

and 2.3 kg of VII dissolved in 24 L of tetrahydrofuran is added. The mixture is agitated at 60° C. When the desired conversion is reached, water, toluene and triethylamine are added to the reaction mixture. After agitation the phases are separated, the aqueous phase is washed with toluene, the combined organic phase is extracted with water. The pH of the combined aqueous phase is set to pH=4-6 with 1M sodium hydrogen sulfate solution. The acidified aqueous phase is extracted with diisopropyl ether. The combined organic phase is washed with 20% sodium chloride solution and after addition of pyridine it is evaporated in vacuum at 45° C. The residue of the evaporation is dried from water by azeotropic distillation with toluene, and then purified by chromatography.

During the chromatographic purification the undesired Z-isomer (VIIIz) is also separated, it is then subjected to double bond isomerisation in UV reactor.

Elution of VIII and VIIIz is carried out using step-gradient mixtures of toluene:methyl tertiary-butyl ether. The eluent mixtures contain pyridine in 0.5% amount by volume.

During the chromatography the undesired Z-isomer is washed off with acetone containing 0.2% amount by volume of acetic acid. To the fraction which contains the Z-isomer triethylamine is added and the solution is concentrated. The concentrate is then diluted with 10-fold amount of methyl tertiary-butyl ether and in order to remove the inorganic salts from the product it is extracted with water, and with saturated salt solution. The organic phase is evaporated (VIIIz isomer).

The concentrated main fraction of compound VIII obtained after chromatographic purification is extracted with 1M potassium carbonate solution, the combined organic phase is washed with methyl tertiary-butyl ether. The pH of the aqueous phase is set to pH=4-6 with 1M sodium hydrogen sulfate solution. The acidified solution is extracted with methyl tertiary-butyl ether. The combined organic phase is washed with 20% sodium chloride solution and after addition of triethylamine it is evaporated in vacuum at 45° C.

Yield: 0.7 kg (41%) VIII, oil. By recycling VIIIz, a further 0.41 kg of intermediate VIII may be prepared, the yield of intermediate VIII is thus 65%.

1f/B. Preparation of VIII by Recycling VIIIz by UV Irradiation

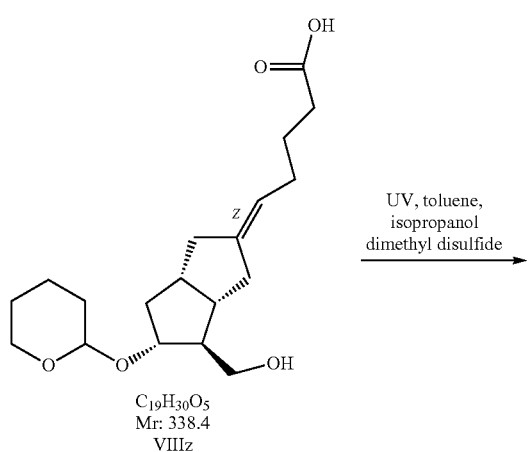

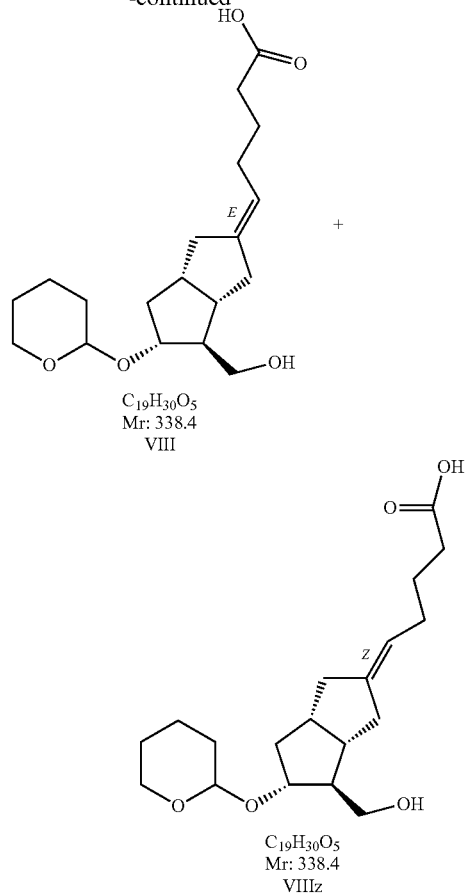

Isomer VIIIz is isomerized by UV irradiation and VIII (E-isomer) is prepared from it in toluene solution in the presence of dimethyl disulfide sensibiliser. The reaction proceeds until the equilibrium ratio is reached and results a 1:1 ratio mixture. Work-up of the reaction mixture and purification is carried out by column chromatography.

Irradiation:

Irradiation is performed in a multi-neck flask under nitrogen atmosphere at 17-19° C. Into the flask 0.99 kg of VIIIz is weighed, then 130.7 ml of methanol and 19.8 L of toluene, and after complete dissolution 99 mL of dimethyl disulfide sensibiliser are added. Cooling is started, the medium-pressure mercury vapour lamp is switched on and the reaction mixture is irradiated for 1.5 hours. The reaction is followed every 15 minute by TLC. When the ratio of the isomers reaches 50:50%, the reaction is terminated. The solution is evaporated at max. 45° C. in a vacuum of max. 10 mbar. The concentrated residue is purified by column chromatography.

Elution is carried out using step-gradient mixtures of toluene:methyl tertiary-butyl ether. The eluent mixtures contain pyridine in 0.5% amount by volume.

The evaporated main fraction of the chromatographic purification is extracted with 1M potassium carbonate solution, the combined aqueous phase is washed twice with methyl tertiary-butyl ether. The pH of the aqueous phase is set to pH=4-6 with 1M sodium hydrogen sulfate solution. The acidified solution is extracted with methyl tertiary-butyl ether. The combined organic phase is washed with 20% sodium chloride solution and after addition of triethylamine it is evaporated in vacuum at 45° C.

Yield: 0.41 kg (41%), oil.

1g. Preparation of [3aS-(2E,3α,4,5,6α)]5-[hexahydro-4-(hydroxymethyl)-5-[(tetrahydro-2H-pyran-2-yl)oxy]-2(1H)-pentalenylidene]pentanoic acid methyl ester (IX)

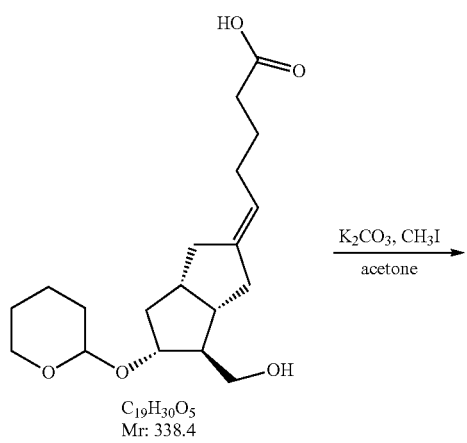

1h. Preparation of (5E)-5-[(3aS,4R,5R,6aS)-5-[(tetrahydro-2H-pyran-2-yl)oxy]-4-[(1E,3S,4RS)-4-methyl-3-oxo-octen-6-in-1-yl]hexahydropentalen-2(1H)-ylidene]pentanoic acid methyl ester (XI)

A. Method: Pfitzner Moffatt Oxidation Followed by One-Pot HWE Reaction

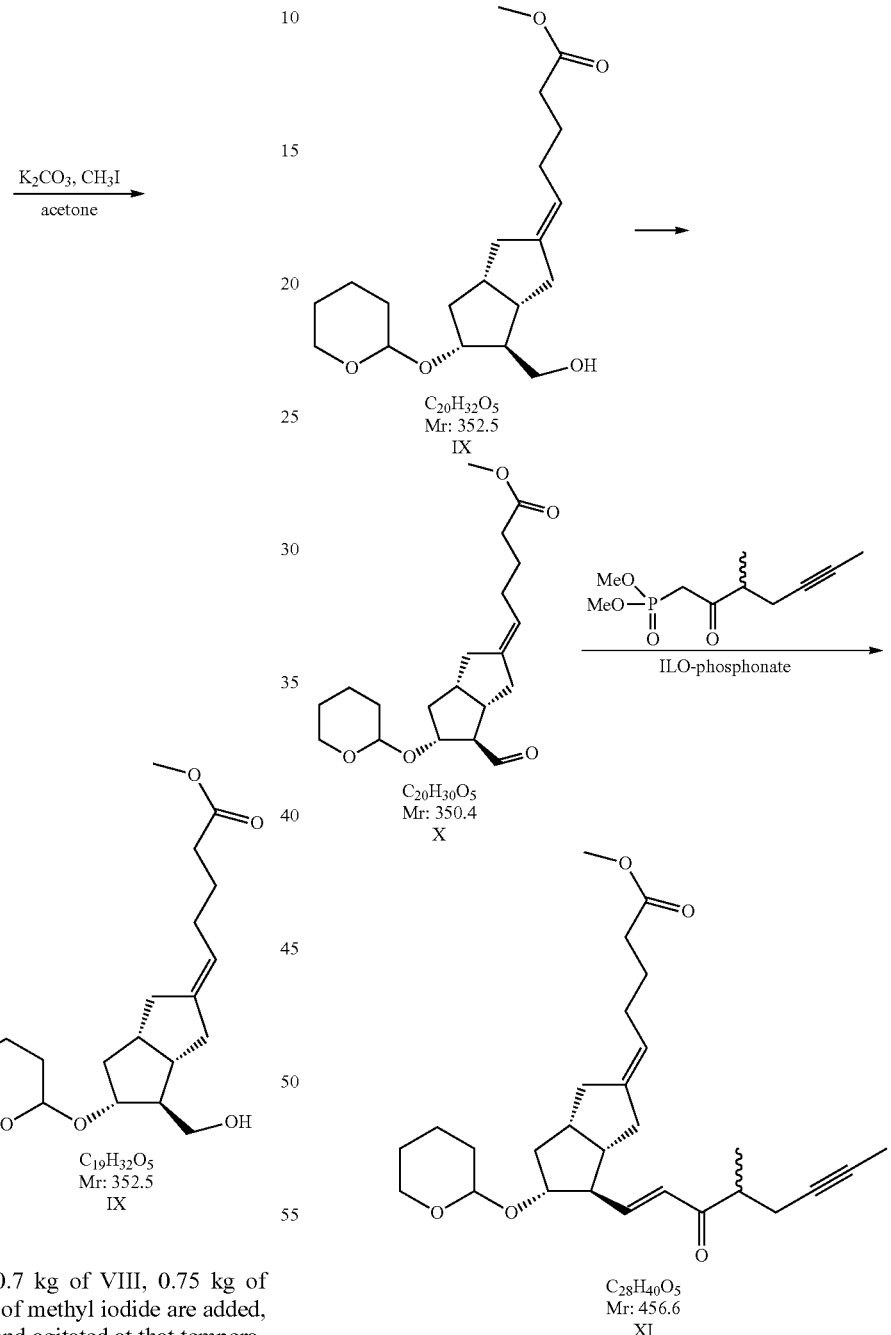

To the acetone solution of 0.7 kg of VIII, 0.75 kg of potassium carbonate and 1.4 kg of methyl iodide are added, the mixture is heated to 45° C. and agitated at that temperature. When the desired conversion is reached the reaction mixture is cooled to room temperature, diluted with water and extracted with methyl tertiary-butyl ether. The combined organic phase is washed with 20% sodium chloride solution and after adding triethylamine it is evaporated in vacuum, at 45° C.

Yield: 0.69 kg (95%), oil.

282 g of IX is dissolved in 1 L of distilled toluene under inert atmosphere. The reaction mixture is cooled to 13° C., 473 g of dicyclohexylcarbodiimide dissolved in 1.5 L of toluene and then 238 mL of 1M phosphoric acid in DMSO solution are added. The reaction is heated to 45° C. and agitated at that temperature. After reaching the desired conversion the reaction mixture which contains the obtained X aldehyde* is cooled to room temperature and under inert atmosphere 78 g of potassium hydroxide and 218 g of ILO-phosphonate dissolved in 1 L of tetrahydrofuran are added. The reaction is agitated while keeping the temperature. When the desired conversion is reached perfil is added to the reaction mixture, it is then filtered off, the solid filtrate is washed with toluene, the liquid filtrate is concentrated in vacuum at 50° C. The concentrated residue, after addition of n-hexane, is purified by chromatography using silica gel column and step-gradient mixtures of toluene:diisopropyl ether. The evaporated main fraction is further purified by repeated chromatography.

*if desired, the aldehyde X may be isolated by chromatographic purification.

Yield: 282 g (77%), oil.

$^{13}C$ and $^1H$ NMR data of compound of formula XI is shown in FIG. 6.

B. Method: Oxidation by DMSO-Phosphoric Acid and DIC, Followed by One-Pot HWE Reaction 28 g of IX is dissolved in 100 mL of distilled toluene under inert atmosphere. The reaction mixture is cooled to 13° C., 50 g of diisopropyl carbodiimide dissolved in 150 mL of toluene and 24 mL of 1M phosphoric acid in DMSO solution are added. After the addition the reaction mixture is heated to 45° C. and agitated at that temperature. After reaching the desired conversion the reaction mixture is cooled to room temperature, under inert atmosphere 8 g of potassium hydroxide and 22 g of ILO-phosphonate dissolved in 100 mL of tetrahydrofuran are added. The reaction is agitated while keeping the temperature. When the desired conversion is reached perfil is added to the reaction mixture, then filtered off and the filtered solid is washed with toluene. The liquid filtrate is concentrated in vacuum at 50° C., the residue, after addition of n-hexane, is purified by chromatography using silica gel column and step-gradient mixtures of toluene:diisopropyl ether. The evaporated main fraction is further purified by repeated chromatography.

Yield: 27 g (74%), oil.

C. Method: Anelli Oxidation (TEMPO and Sodium Hypochlorite)

The oxidant solution is prepared from 100 mL of water, 100 mL of 5% sodium hypochlorite solution and 36 g of sodium bicarbonate. The pH of the solution is 9.4±0.2. If the pH>9.6, it is adjusted with sodium bicarbonate.

6 g of IX is dissolved in 70 mL of dichloromethane (DCM), then 0.01 g of TEMPO catalyst and 0.2 g of potassium bromide are added. The mixture is cooled to 0° C. and the oxidant solution is added to it at a rate that the temperature remains below 10° C. Expected reaction time 30 minutes.

The reaction mixture is then quenched with 10% sodium thiosulfate solution, agitated at 10-15° C. for 30 minutes. The aqueous phase is extracted 3-times with DCM. The organic phases are combined and washed with 15% sodium chloride solution.

Under inert atmosphere 20 mL of 1M sodium hydroxide solution and 4 g of ILO-phosphonate dissolved in 20 mL of tetrahydrofuran are added. The reaction mixture is agitated while keeping the temperature. At the end of the reaction the phases are separated, the organic phase is washed sequentially with 1M sodium hydrogen sulfate solution, 15% sodium chloride solution and saturated salt solution. The organic phase is concentrated in vacuum at 45° C. The residue is, after the addition of n-hexane, purified by chromatography using silica gel column and step-gradient mixtures of toluene:diisopropyl ether. The evaporated main fraction is further purified by repeated chromatography.

Yield: 5.75 g (74%), oil.

Preparation of (5E)-5-[(3aS,4R,5R,6aS)-4-formyl-5-tetrahydropyran-2-yloxy-3,3a,4,5,6,6a-hexahydro-1H-pentalen-2-ylidene]pentanoic acid methyl ester (X)

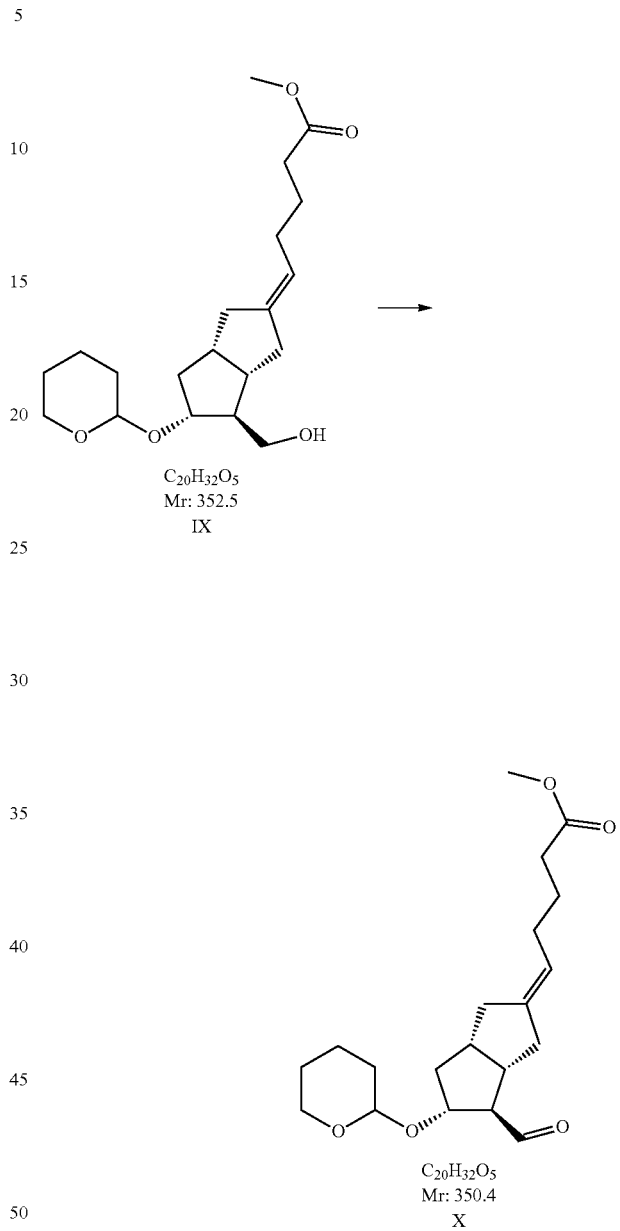

28.2 g of IX is dissolved in 100 mL of distilled toluene under inert atmosphere. The reaction mixture is cooled to 13° C., then 47.3 g of dicyclohexylcarbodiimide dissolved in 150 mL of toluene, and 23.8 mL of 1M phosphoric acid in DMSO solution are added. After the addition the reaction mixture is heated to 45° C. and agitated at that temperature. After reaching the desired conversion the reaction mixture is cooled to room temperature, washed with water (2×300 mL), the organic phase is dried from water by concentration in vacuum at 50° C. to approx. 80 mL volume. The toluene concentrate is purified by chromatography using silica gel column and toluene, toluene:diisopropyl ether=3:1 and 1:1 eluent mixtures. The fractions containing the aldehyde X are combined and evaporated.

Yield: 23.82 g (85%).

1i. Preparation of methyl (5E)-5-[(3aS,4R,5R)-5-hydroxy-4-[(E,3S)-3-hydroxy-4-methyl-oct-1-en-6-inyl]-3,3a,4,5,6,6a-hexahydro-1H-pentalen-2-ylidene]pentanoate (XIII)

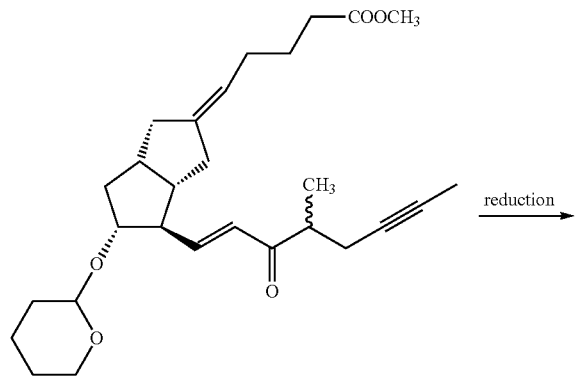

C$_{28}$H$_{40}$O$_5$
Mr: 456.6
XI reduction

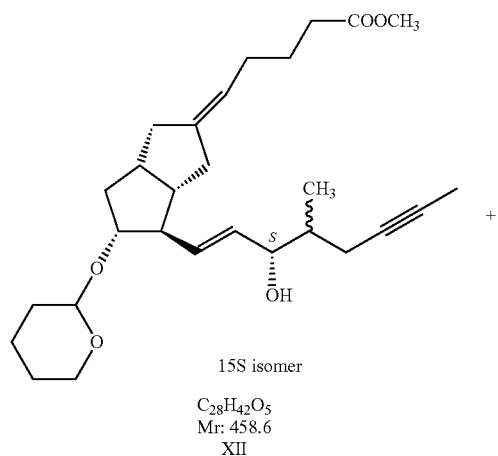

15S isomer
C$_{28}$H$_{42}$O$_5$
Mr: 458.6
XII

+

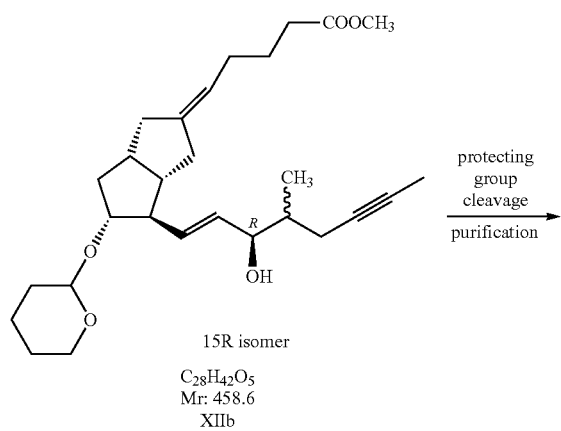

15R isomer
C$_{28}$H$_{42}$O$_5$
Mr: 458.6
XIIb protecting group cleavage
purification

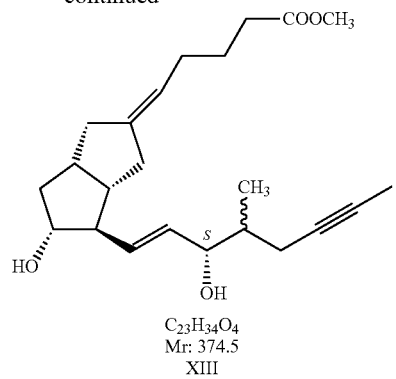

C$_{23}$H$_{34}$O$_4$
Mr: 374.5
XIII

To prepare the DIBAL-F reagent 350 g of di-tert-butyl-methylphenol is dissolved in 650 mL of distilled toluene under inert atmosphere, at room temperature, and to the obtained solution the toluene solution of 102.8 g of diisobutylaluminum hydride (DIBAL-H) is added. The reagent is prepared at 0° C., but at the end of the addition the reaction mixture is agitated for 1 hour at room temperature, then for 6 hours at 45° C., under inert atmosphere. The reagent mixture is then cooled to 5° C. and under inert atmosphere 94 g of XI in toluene solution is added. During the addition the temperature is elevating. The reaction mixture is agitated at room temperature until the desired conversion is reached, then quenched with 2M sodium hydrogen sulfate solution. The quenched mixture is extracted with toluene to obtain the protected enol isomers XII* and XIIb which are reacted further without isolation. To the combined organic phase the methanol solution of 7.05 g of p-toluenesulfonic acid is added. The reaction mixture is agitated at room temperature. After reaching the desired conversion the pH of the reaction mixture is set to pH>7.5 with triethylamine and concentrated in vacuum, at 45° C. The concentrated residue is dissolved in n-hexane and purified by chromatography using silica gel column and step-gradient mixtures of n-hexane:ethyl acetate.

*If desired, the protected enol XII may be isolated by chromatographic purification.

Yield: 43.1 g (56%), oil.

Purification of XIII by Preparative HPLC 50 g of XIII is dissolved in 100 mL of acetonitrile, to the solution water is dropped until the acetonitrile:water=3:1 ratio is reached. The stock-solution is filtered through a pre-column made of 5 g 10 micron particle size and 120 Angström pore size C18 reverse phase silica gel. The filtered stock-solution is purified by high pressure preparative liquid chromatography using 400 g of 10 micron particle size and 120 Angström pore size C18 reverse phase silica gel packing and water:acetone eluent mixtures. The combined main fraction of the chromatography is concentrated in vacuum at 40° C., the concentrated solution is extracted with methyl tertiary-butyl ether, the combined organic phase is washed with salt solution, dried over sodium sulfate and evaporated in vacuum at 30° C.

Yield of the preparative HPLC: 32 g (64%), oil.

Preparation of XI from XIIIb

Oxidation of XIIIb to XIb and THP-Protection

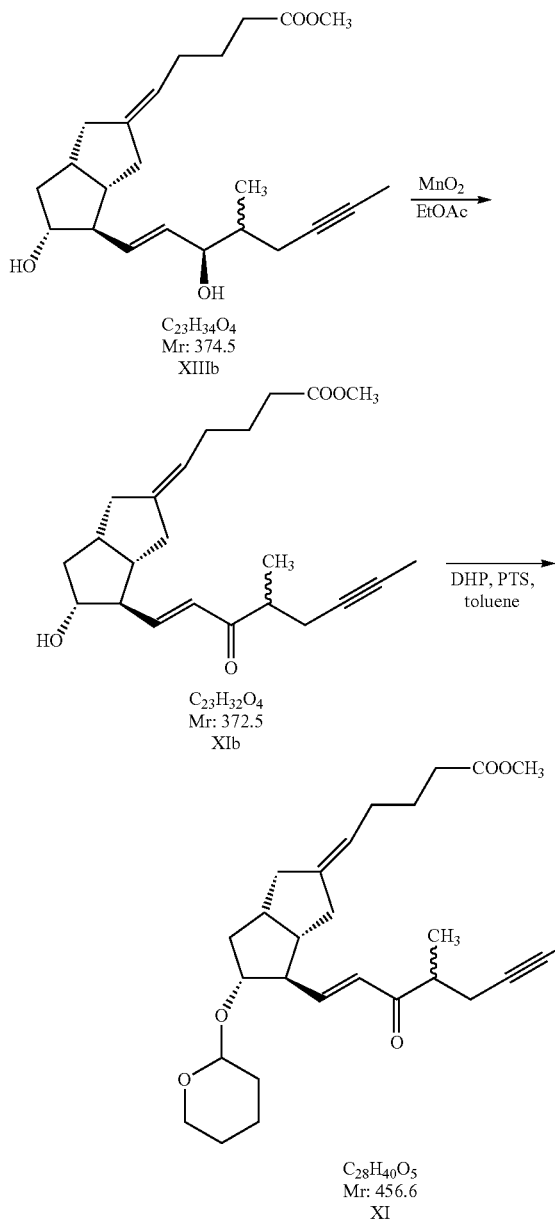

Preparation of (5E)-5-[(3aS,4R,5R,6aS)-4-[(E)-3S-hydroxy-4-methyl-oct-1-en-6-inyl]-5-tetrahydropyran-2-yloxy-3,3a,4,5,6,6a-hexahydro-1H-pentalen-2-ylidene]pentanoic acid methyl ester (XII)

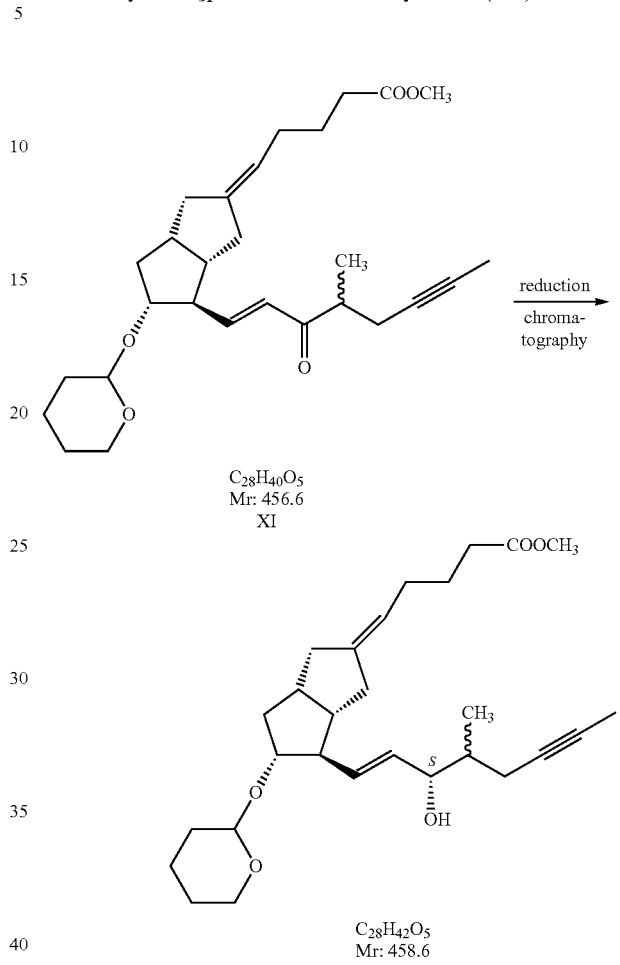

7 g of XIIIb is dissolved in 75 mL of ethyl acetate and filtered through a filter-bed made of 110 g of activated MnO$_2$, wetted with ethyl acetate. The filtrate is repeatedly let through the filter-bed. The MnO$_2$ bed is washed twice with ethyl acetate previously saturated with water.

The conversion is checked with TLC, if it is not sufficient, the filtrate is repeatedly filtered through a fresh MnO$_2$ filter-bed. The filtrate is evaporated, the obtained crude product is dried from water by distilling off toluene. To the concentrate 100 mL of toluene, 4 g of dihydropyran and 0.01 g of para-toluenesulfonic acid are added, the THP-protection is followed by TLC. At the end of the reaction it is stopped by addition of triethylamine, the reaction mixture is poured onto water, the organic phase is extracted twice with water, then the organic phase is evaporated.

Yield: 4.8 g (56.3%), oil. The product may be used in the selective reduction step.

To prepare the DIBAL-F reagent, 35 g of di-tert-butylmethylphenol is dissolved in 65 mL of distilled toluene under inert atmosphere, at room temperature. To the obtained solution the toluene solution of 10.3 g of diisobutylaluminum hydride (DIBAL-H) is added. The reagent is prepared at 0° C., but at the end of the addition the reaction mixture is agitated for 1 hour at room temperature, then for 6 hours at 45° C., under inert atmosphere. The reagent mixture is cooled to 5° C. and under inert atmosphere 9.4 g of XI in toluene solution is added. During the addition the temperature of the mixture is elevating. The reaction mixture is agitated at room temperature until the desired conversion is reached, then it is quenched with 2M sodium hydrogen sulfate solution. The quenched reaction mixture is extracted with toluene. The toluene phase is concentrated in vacuum at 50° C. to about 30 mL. The concentrated toluene residue is purified by chromatography using silica gel column and step-gradient mixtures of n-hexane:ethyl acetate. The fractions containing the protected enol XII are combined, the combined main fraction is evaporated.

Yield: 7.22 g (76.5%).

1j. Preparation of Crude Iloprost 43.1 g of XIII is dissolved in 22 mL of tetrahydrofuran under inert atmosphere at room temperature, then 520 mL of 1M sodium hydroxide solution is added to it, at a rate that the temperature of the reaction mixture remains between 20-30° C. After reaching the desired conversion the phases are separated, the aqueous phase is extracted twice with methyl tertiary-butyl ether, the organic phases are combined and washed twice with 1M sodium hydroxide solution. The combined alkaline phase is diluted with methyl tertiary-butyl ether and under agitation the pH is set to pH 3 with 2M sodium hydrogen sulfate solution. The acidified aqueous phase is extracted with methyl tertiary-butyl ether, the combined organic phase is washed with 20% sodium chloride solution and evaporated in vacuum, at 30° C.

Purity of the product is 93%, total amount of related impurities is not more than 5%, total amount of other, non-identified impurities is not more than 4%.

From this material it is not possible to prepare the solid form of iloprost because of the level of purity detailed above.

1k. Purification of Crude Iloprost by Gravitational Chromatography and Solidification Purification of Crude Iloprost, Method B.

64.5 g of crude iloprost is dissolved in 25 mL of dist. acetone, to the solution approx. 50 mL of n-pentane is added until it turns opalescent, then it is purified on gravitational column packed with Si6 normal phase (particle size 0.063-0.2 mm) silica gel, using step-gradient mixtures of n-pentane:acetone. The fractions are combined after investigation by TLC. The main fraction solution is filtered through a 5 micron teflon membrane and then evaporated in vacuum at max. 35° C. bath temperature.

To 50 g of the chromatographed iloprost phase-product 200 mL of filtered, dist. acetone is added. The mixture is shaken at 20-25° C. till complete dissolution, then under continuous shaking 1080 mL of filtered pentane is added to the solution, wherein iloprost fully precipitates from the mixture in the form of oil.

The mixture is cooled without agitation to (−)60° C., after 6 hours it is allowed to warm to (−)20° C. and kept at that temperature without agitation for at least 16 hours. The solvent is then removed from the oily crystal mass by decantation, 650 mL of filtered pentane is poured onto the product, and the crystal mass is kept at (−)20° C. for minimum 2 hours. The solvent is again removed by decantation.

The solvent is distilled off from the product in high vacuum at (−)30° C., the temperature is kept between (−)20-(−)30° C. During removal of the solvent the solid product is stirred through from time to time. Solvent removal is performed under inert atmosphere, it takes approx. 120 hours.

Purity of the product is 95.0%, total amount of related impurities is not more than 3.5%, total amount of other, non-identified impurities is not more than 2.5%.

1l. Purification of Crude Iloprost by Preparative HPLC, Followed by Filtration Through Silica Gel and Solidification Purification of Crude Iloprost, Method C.

64.5 g of crude iloprost is dissolved in 100 mL of acetonitrile, to the solution water is dropped until the acetonitrile:water=3:1 ratio is reached. The stock-solution is filtered through a pre-column made of 5 g 10 micron particle size and 120 Angström pore size C18 reverse phase silica gel. Purification of the filtered stock-solution is carried out by high pressure preparative liquid chromatography using 400 g of 10 micron particle size and 120 Angström pore size C18 reverse phase silica gel packing and water:acetonitrile eluent mixtures. The combined main fraction of the chromatography is concentrated in vacuum at 40° C., the concentrated solution is extracted with methyl tertiary-butyl ether, the combined organic phase is washed with saturated salt solution, dried over sodium sulfate and concentrated in vacuum at 30° C. to 100 mL. The concentrated solution is completed with acetone to 150 g, carefully n-pentane is added until it turns slightly opalescent. The obtained solution is further purified by filtration through silica gel using step-gradient mixtures of n-pentane:acetone. The main fraction is evaporated at 30° C. in high vacuum.

To 50 g of iloprost phase-product purified by preparative HPLC and filtered through silica gel, 200 mL of filtered, dist. acetone is added. The mixture is shaken at room temperature till complete dissolution, then 1080 mL of filtered pentane is added, wherein iloprost fully precipitates from the mixture, in the form of oil.

The mixture is cooled without agitation to (−)60° C., after 6 hours it is allowed to warm to (−)20° C. and kept at that temperature without agitation for at least 16 hours. The solvent is then removed from the oily crystal mass by decantation, 650 mL of filtered pentane is poured on it and the crystal mass is kept at (−)20° C. for minimum 2 hours. The solvent is removed again by decantation.

The solvent is distilled off from the product in high vacuum at (−)30° C., the temperature is kept between (−)20-(−)30° C. During this removal of solvent the solid product is stirred through from time to time. Solvent removal is performed under inert atmosphere, it takes approx. 120 hours.

Purity of the product is 98.0%, total amount of related impurities is not more than 1.6%, total amount of other, non-identified impurities is not more than 1.0%.

| Related impurities (HPLC) | |
|---|---|
| Iloprost Z-isomers, total | ≤0.60% |
| other impurities, total of which | ≤1.0% |
| 15-epi-Iloprost | ≤0.20% |
| 15-oxo-Iloprost | ≤0.20% |
| Iloprost-methyl ester | ≤0.10% |
| Iloprost-ethyl ester | ≤0.10% |
| Iloprost dimer 1 | ≤0.20% |
| Iloprost dimer 2 | ≤0.20% |
| non-identified impurities, each | ≤0.10% |

1m. Purification of Crude Iloprost by Gravitational and Preparative HPLC Chromatographies, Filtration Through Silica Gel and Solidification Purification of Crude Iloprost, Method D.

80 g of crude iloprost is dissolved in 40 mL of dist. acetone, approx. 70 mL of n-pentane is added until the solution turns opalescent, then it is purified on gravitational column packed with Si60 normal phase (particle size 0.063-0.2 mm) silica gel, using step-gradient mixtures of n-pentane:acetone. The fractions are combined after investigation by TLC. The main fraction solution is filtered through a 5 micron teflon membrane and evaporated in vacuum at max. 35° C. bath temperature.

60 g of crude iloprost phase-product purified by gravitational chromatography, is dissolved in 110 mL of acetonitrile, to the solution water is dropped until the acetonitrile:water=3:1 ratio is reached. The stock-solution is filtered through a pre-column made of 5 g 10 micron particle size and 120 Angström pore size C18 reverse phase silica gel. Purification of the filtered stock-solution is carried out by high pressure preparative liquid chromatography using 400 g of 10 micron particle size, 120 Angström pore size C18 reverse phase packing and water:acetonitrile mixtures as eluent. The combined main fraction of the chromatography is concentrated in vacuum at 40° C., the concentrated solution is extracted with methyl tertiary-butyl ether, the combined organic phase is washed with saturated salt solution, dried over sodium sulfate and concentrated to 100 mL in vacuum at 30° C. The concentrated solution is completed with acetone to 150 g, then carefully n-pentane is added until it turns slightly opalescent and then filtered through silica gel. The main fraction is evaporated in high vacuum, at 30° C.

To 50 g of iloprost phase-product purified by preparative HPLC and filtered through silica gel, 200 mL of filtered, dist. acetone is added. The mixture is shaken at room temperature till complete dissolution, then 1080 mL of filtered pentane is added, wherein iloprost fully precipitates from the mixture, in the form of oil.

The mixture is cooled without agitation to (–)60° C., after 6 hours it is allowed to warm to (–)20° C. and kept at that temperature without agitation for at least 16 hours. The solvent is then removed from the oily crystal mass by decantation, 650 mL of filtered pentane is poured onto the product and the crystal mass is kept at (–)20° C. for minimum 2 hours. The solvent is removed again by decantation.

The solvent is distilled off from the product in high vacuum at (–)30° C., keeping the temperature between (–)20-(–)30° C. During solvent removal the solid product is stirred through from time to time. Solvent removal is carried out under inert atmosphere, it takes approx. 120 hours.

The solid product obtained is a powder that crystallizes on standing.

Purity of the obtained product is 98.5%, total amount of related impurities is not more than 1.6%, total amount of other, non-identified impurities is not more than 0.5%.

X-ray powder diffractogram is shown in FIG. 1, DSC curve in FIG. 3, $^{13}C$ and $^{1}H$ NMR data in FIG. 5. The XRPD pattern of the product contains characteristic peaks at the following values (degrees±0.2° 2-theta): 5.43, 7.51, 7.81, 15.19, 15.57, 15.85, 16.25, 16.84, 17.08, 17.26, 18.14, 18.59, 19.17, 20.32, 20.53, 21.69, 22.12, and 23.28

| Related impurities (HPLC) | |
|---|---|
| Iloprost Z-isomers, total | ≤0.60% |
| other impurities, total of which | ≤1.0% |
| 15-epi-Iloprost | ≤0.10% |
| 15-oxo-Iloprost | ≤0.20% |
| Iloprost methyl ester | ≤0.20% |
| Iloprost ethyl ester | ≤0.05% |
| Iloprost dimer 1 | ≤0.10% |
| Iloprost dimer 2 | ≤0.10% |
| non-identified impurities, each | ≤0.10% |

1n. Preparation of 16(S)-Iloprost ((S)-I)

A: By Chromatographic Separation and Crystallisation

A1: Chromatography Using Acetonitrile:Water Eluent Mixture

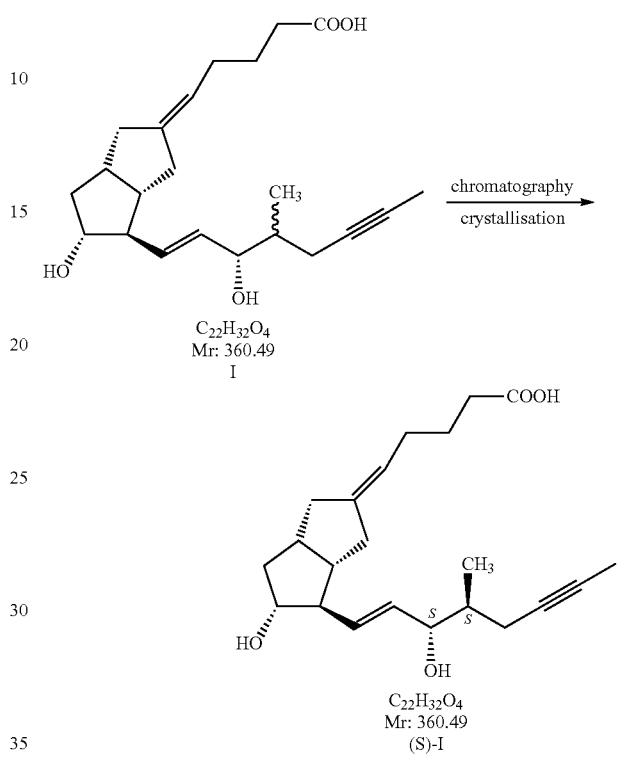

50 g of crude I ((S)-I content: 20 g) is dissolved in 100 mL of acetonitrile and to the solution water is dropped until the acetonitrile:water=3:1 ratio is reached. The stock-solution is filtered through a pre-column made of 5 g 10 micron particle size and 120 Angström pore size C18 reverse phase silica gel. Purification of the filtered stock-solution is carried out by high pressure preparative liquid chromatography using 400 g of 10 micron particle size and 120 Angström pore size C18 reverse phase silica gel packing and water:acetonitrile eluent mixtures.

Of the diastereomers of iloprost, the 16(S)-iloprost diastereomer has higher retention time. By preparative HPLC it may be separated with good efficiency from the 16(R)-iloprost diastereomer eluting before it.

The combined main fraction of 16(S)-iloprost of the chromatography is concentrated in vacuum at 40° C., the concentrated solution is extracted with methyl tertiary-butyl ether, the combined organic phase is washed with saturated salt solution, dried over sodium sulfate and evaporated in vacuum at 30° C. The residue is dissolved in 32 mL of acetone, then carefully n-pentane is added until the solution turns slightly opalescent. The solution thus obtained is further purified by filtrating through silica gel using step-gradient mixtures of n-pentane:acetone. The main fraction is evaporated in high vacuum at 30° C.

To 15 g of 16(S)-iloprost phase-product purified by preparative HPLC and filtered through silica gel, 15 mL of filtered dist. acetone is added. The mixture is shaken at room temperature till complete dissolution, then under continuous shaking 100 mL of filtered pentane is added, until the solution turns opalescent. The mixture is cooled to (−) 40° C. and while keeping that temperature it is agitated under inert atmosphere for 16 hours. The precipitated crystalline material is filtered off.

The product is dried at a temperature between (−)10 and (+10° C. in high vacuum, under inert atmosphere.

Drying takes approx. 120 hours.

Purity of the product is 98.0%, total amount of related impurities is not more than 1.6%, total amount of other, non-identified impurities is not more than 1.0%.

X-ray powder diffractogram is shown in FIG. 2, DSC curve in FIG. 4, $^{13}C$ and $^{1}H$ NMR data in FIG. 9.

The XRPD pattern of the product contains characteristic peaks at the following values (degrees±0.2° 2-theta): 7.46, 7.80, 12.69, 14.91, 15.58, 16.82, 17.27, 20.31, 20.62, 23.30, 28.13, 31.38, 32.05, 34.88, and 38.88.

A2: Chromatography Using Methanol:2-Propanol:Water Eluent Mixture 64.5 g of crude I is dissolved in 100 mL of 2-propanol, to the solution water is dropped until the 2-propanol:water=1:1 ratio is reached. The stock-solution is filtered through a pre-column made of 5 g 10 micron particle size and 120 Angström pore size C18 reverse phase silica gel. Purification of the filtered stock-solution is carried out by high pressure preparative liquid chromatography using 400 g of 10 micron particle size and 120 Angström pore size C18 reverse phase silica gel packing and water:methanol:2-propanol eluent mixtures.

The combined main fraction of the chromatography is concentrated in vacuum at 40° C., the concentrated solution is extracted with methyl tertiary-butyl ether, the combined organic phase is washed with saturated salt solution, dried over sodium sulfate and evaporated in vacuum, at 30° C. The residue is dissolved in 32 mL of acetone and carefully n-pentane is added until the solution turns slightly opalescent. The solution thus obtained is further purified by filtrating through silica gel using step-gradient mixtures of n-pentane:acetone. The main fraction is evaporated in high vacuum at 30° C.

To 15 g of 16(S)-iloprost phase-product purified by preparative HPLC and filtered through silica gel, 15 mL of filtered dist. acetone is added. The mixture is shaken at room temperature till complete dissolution, then 100 mL of filtered pentane is added until the solution turns opalescent. The mixture is cooled to (−)40° C. and while keeping that temperature it is agitated under inert atmosphere for 16 hours. The precipitated crystalline material is filtered off.

The product is dried at a temperature between (−)10 and (+10° C. in high vacuum, under inert atmosphere.

Drying takes approx. 120 hours.

Purity of the product is 98.0%, total amount of related impurities is not more than 1.6%, total amount of other, non-identified impurities is not more than 1.0%.

1o. Preparation of 16(S)-Iloprost by Chemical Synthesis (5E)-5-[(3aS,4R,5R,6aS)-5-[(tetrahydro-2H-pyran-2-yl)oxy]-4-[(1E,4S)-4-methyl-3-oxo-octen-6-in-1-yl]hexahydropentalen-2(1H)-ylidene]pentanoic acid methyl ester ((S)-XI)

B: By Chemical Synthesis

B1: Pfitzner Moffatt Oxidation Followed by One-Pot HWE Reaction

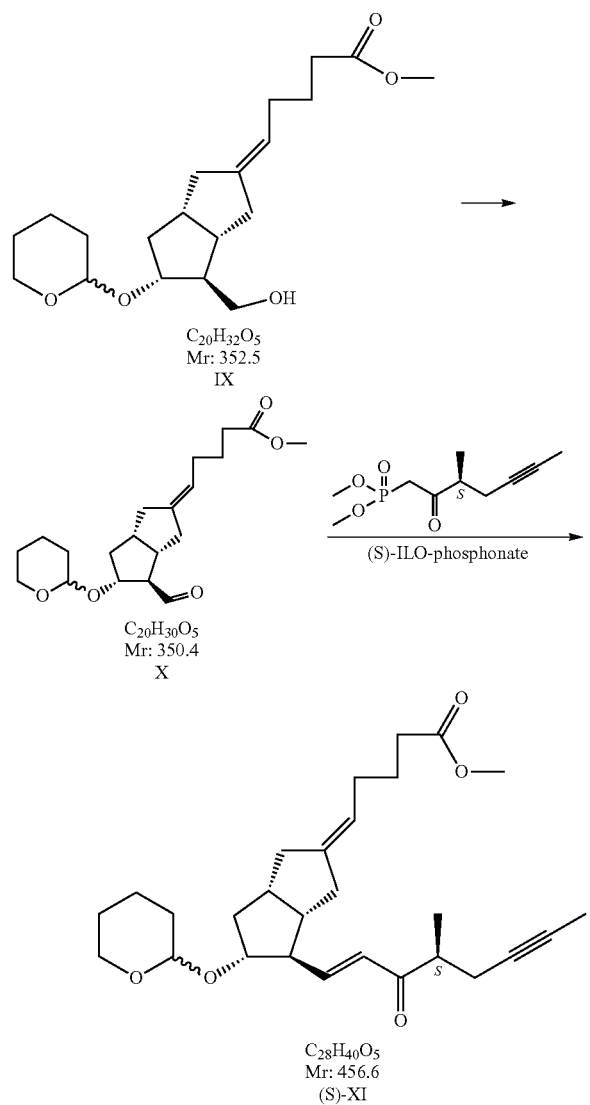

140 g of IX is dissolved in 1 L of distilled toluene under inert atmosphere. The reaction mixture is cooled to 13° C. and the solution of 235 g of dicyclohexylcarbodiimide in 0.75 L of toluene and 118 mL of 1M phosphoric acid in DMSO solution are added. After addition the reaction is heated to 45° C. and agitated at that temperature. After reaching the desired conversion the reaction mixture containing the obtained X aldehyde is cooled to room temperature, under inert atmosphere 39 g of potassium hydroxide and 109 g of (S)-ILO-phosphonate (optically active) dissolved in 0.5 L of tetrahydrofuran are added. The reaction mixture is agitated while keeping the temperature. When the desired conversion is reached, perfil is added to the reaction mixture, then it is filtered off, the filtered solid is washed with toluene, the liquid filtrate is concentrated in vacuum at 50° C. The concentrated residue, after addition of n-hexane, is purified by chromatography using silica gel column and step-gradient mixtures of toluene:diisopropyl ether. The evaporated main fraction is further purified by repeated chromatography.

Yield: 140 g (77%), oil.

$^{13}$C and $^1$H NMR data of compound of formula (S)-XI is shown in FIG. 7.

B2: Anelli Oxidation (TEMPO and Sodium Hypochlorite)

The oxidant solution is prepared from 100 mL of water, 100 mL of 5% sodium hypochlorite and 36 g of sodium bicarbonate. The pH of the solution is 9.4±0.2. If the pH>9.6, it is adjusted with sodium bicarbonate.

6 g of IX is dissolved in 70 mL of dichloromethane (DCM), then 0.01 g of TEMPO catalyst and 0.2 g of potassium bromide are added. The mixture is cooled to 0° C. and the oxidant solution is added to it at a rate that the temperature remains below 10° C. Expected reaction time is 30 minutes.

The reaction mixture is then quenched with 10% sodium thiosulfate solution, agitated at 10-15° C. for 30 minutes. The aqueous phase is extracted 3-times with DCM. The organic phases are combined and washed with 15% sodium chloride solution.

Under inert atmosphere 20 mL of 1M sodium hydroxide solution and 4 g of (S)-ILO-phosphonate dissolved in 20 mL of tetrahydrofuran are added. The reaction is agitated while keeping the temperature. At the end of the reaction the phases are separated, the organic phase is washed sequentially with 1M sodium hydrogen sulfate solution, 15% sodium chloride solution and saturated salt solution. The organic phase is concentrated in vacuum at 45° C. The residue, after the addition of n-hexane, is purified by chromatography using silica gel column and step-gradient mixtures of toluene:diisopropyl ether. The evaporated main fraction is further purified by repeated chromatography.

Yield: 5.75 g (74%), oil.

1p. Preparation of methyl (5E)-5-[(3aS,4R,5R)-5-hydroxy-4-[(E,3S,4S)-3-hydroxy-4-methyl-oct-1-en-6-inyl]-3,3a,4,5,6,6a-hexahydro-1H-pentalen-2-ylidene]pentanoate ((S)-XIII)

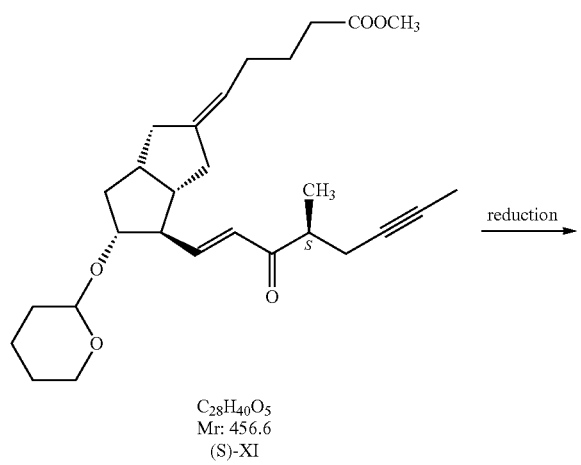

To prepare the DIBAL-F reagent 350 g of di-tert-butyl methylphenol is dissolved in 650 mL of distilled toluene at room temperature, under inert atmosphere, and to the obtained solution the toluene solution of 102.8 g of diisobutylaluminum hydride (DIBAL-H) is added. The reagent is prepared at 0° C., but at the end of the addition the reaction mixture is agitated for 1 hour at room temperature, then for 6 hours at 45° C., under inert atmosphere. The reagent mixture is then cooled to 5° C. and under inert atmosphere 94 g of (S)-XI in toluene solution is added. During the addition the temperature is elevating. The reaction mixture is agitated at room temperature until the desired conversion is reached, then quenched with 2M sodium hydrogen sulfate solution. The quenched reaction mixture is extracted with toluene to obtain the protected enol isomers (S)-XII* and 15-epi-(S)-XII which are reacted further without isolation. To the combined organic phase the methanol solution of 7.05 g of p-toluenesulfonic acid is added. The reaction mixture is agitated at room temperature. When the desired conversion is reached, the pH of the reaction mixture is set to pH>7.5 with triethylamine and it is concentrated in vacuum at 45° C. The residue is dissolved in n-hexane and purified by chromatography using silica gel column and step-gradient mixtures of n-hexane:ethyl acetate.

*If desired, the protected enol, (S)-XII may be isolated by chromatographic purification.

Yield: 43.1 g (56%), oil.

$^{13}$C and $^1$H NMR data of compound of formula (S)-XII is shown in FIG. 8.

Preparation of Crude 16(S)-Iloprost

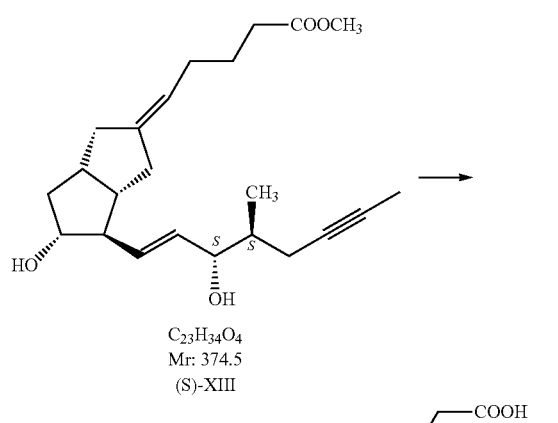

$C_{23}H_{34}O_4$
Mr: 374.5
(S)-XIII

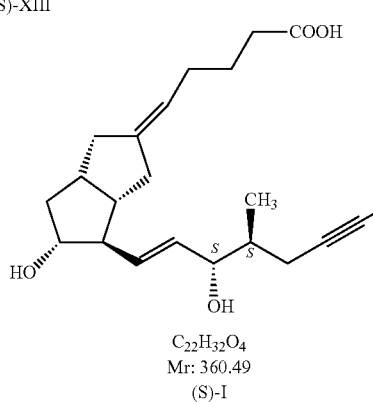

$C_{22}H_{32}O_4$
Mr: 360.49
(S)-I 43.1 g of (S)-XIII is dissolved in 50 mL of tetrahydrofuran at room temperature, under inert atmosphere. To the solution 520 mL of 1M sodium hydroxide solution is added at a rate that the temperature of the reaction mixture remains between 20-30° C. After reaching the desired conversion the phases are separated, the aqueous phase is extracted twice with methyl tertiary-butyl ether, the organic phases are combined and washed twice with 1M sodium hydroxide solution. The combined alkaline phase is diluted with methyl tertiary-butyl ether and under agitation the pH is set to pH 3 with 2M sodium hydrogen sulfate solution. The acidified aqueous phase is extracted with methyl tertiary-butyl ether, the combined organic phase is washed with 20% sodium chloride solution and evaporated in vacuum at 30° C.

Purity of the product is 93%, total amount of related impurities is not more than 5%, total amount of other, non-identified impurities is not more than 4%.

Purity of this material already allows to prepare the solid 16(S)-iloprost.

Purification of Crude 16(S)-Iloprost by Gravitational Chromatography and Crystallisation 40.2 g of crude 16(S)-iloprost is dissolved in 60 mL of acetone and carefully n-pentane is added until the solution turns slightly opalescent. The obtained solution is purified by filtration through silica gel using step-gradient mixtures of n-pentane:acetone. The main fraction is evaporated in high vacuum at 30° C.

To 37 g of 16(S)-iloprost phase-product, filtered through silica gel, 12 mL of filtered dist. acetone is added. The mixture is shaken at room temperature till complete dissolution, then under continuous shaking 90 mL of filtered pentane is added, until the solution turns opalescent. The mixture is cooled to (−)40° C. and while keeping that temperature it is agitated under inert atmosphere for 16 hours. The precipitated crystalline material is filtered off.

The product is dried in high vacuum at a temperature between (−)10° C. and (+10° C. under inert atmosphere. Drying takes approx. 120 hours.

Purity of the product is 98.0%, total amount of related impurities is not more than 1.6%, total amount of other, non-identified impurities is not more than 1.0%.

1g. Preparation of (R)-Iloprost ((R)-I) by Chemical Synthesis

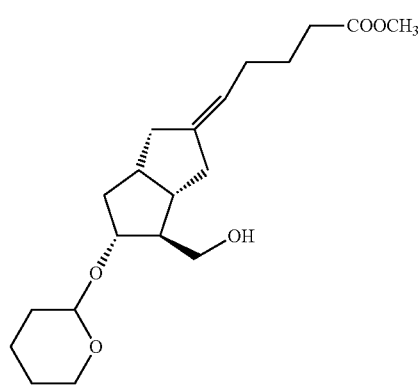

$C_{20}H_{32}O_5$
Mr: 352.5
IX

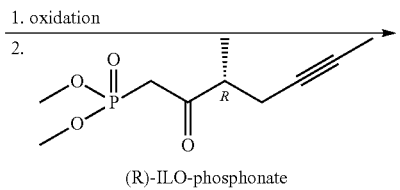

(R)-ILO-phosphonate

-continued

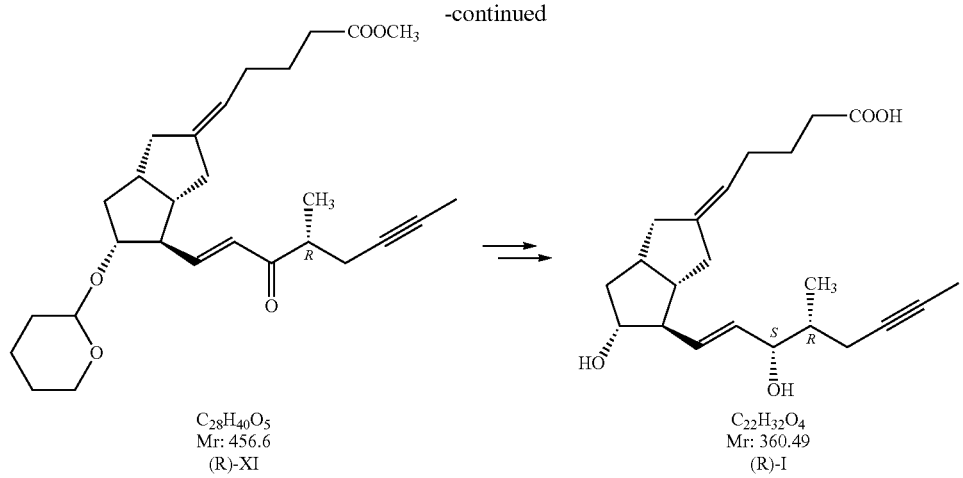

C<sub>28</sub>H<sub>40</sub>O<sub>5</sub>
Mr: 456.6
(R)-XI

C<sub>22</sub>H<sub>32</sub>O<sub>4</sub>
Mr: 360.49
(R)-I

Starting from the toluene solution of 140 mg of (R)-IX, carrying out the above described chemical steps using (R)-ILO-phosphonate, 51.1 mg of 16(R)-iloprost was prepared.

The invention claimed is:

1. Process for the preparation of the solid form of the compound of formula I

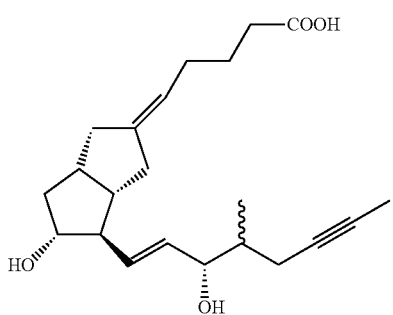

I comprising that (step 1) the purified oily compound of formula I is dissolved in the same amount of polar solvent as the mass of the oily product, and (step 2) such an amount of alkane is added to the solution of step 1 that the solution turns opalescent, (step 3) the solution is then solidified glassy at a temperature from −60° C. to −20° C. and the solvent is removed in high vacuum.

2. Process according to claim 1 wherein the polar solvent is acetone, ethyl acetate, methyl ethyl ketone or isopropanol and wherein the alkane is pentane, n-hexane, cyclohexane or heptane.

3. Solid phase iloprost in the form of amorphous powder.

4. Crystalline 16(S)-iloprost.

5. Iloprost having a purity of at least 98.5 mass % in the form of a crystal.

\* \* \* \* \*